United States Patent
Bhambhani et al.

(10) Patent No.: US 10,617,650 B2
(45) Date of Patent: Apr. 14, 2020

(54) PROCESS FOR PREPARING FORMULATIONS FOR GASTROINTESTINAL-TARGETED THERAPIES

(71) Applicant: Merck Sharp & Dohme Corp., Rahway, NJ (US)

(72) Inventors: Akhilesh Bhambhani, Doylestown, PA (US); Robert K. Evans, Souderton, PA (US); Pranav Gupta, Basking Ridge, NJ (US); Ronald L. Smith, Yardley, PA (US); Donna M. Williams, Glenside, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 15 days.

(21) Appl. No.: 15/768,044

(22) PCT Filed: Oct. 11, 2016

(86) PCT No.: PCT/US2016/056322
§ 371 (c)(1),
(2) Date: Apr. 13, 2018

(87) PCT Pub. No.: WO2017/066134
PCT Pub. Date: Apr. 20, 2017

(65) Prior Publication Data
US 2018/0311172 A1     Nov. 1, 2018

Related U.S. Application Data

(60) Provisional application No. 62/242,718, filed on Oct. 16, 2015.

(51) Int. Cl.
*A61K 9/50* (2006.01)
*A61K 9/00* (2006.01)
*A61K 9/16* (2006.01)

(52) U.S. Cl.
CPC .......... *A61K 9/5026* (2013.01); *A61K 9/0053* (2013.01); *A61K 9/5042* (2013.01); *A61K 9/5089* (2013.01); *A61K 9/1652* (2013.01)

(58) Field of Classification Search
CPC .... A61K 9/5089; A61K 9/5042; A61K 9/005; A61K 9/5026; A61K 9/1623; A61K 9/1652
See application file for complete search history.

(56) References Cited

U.S. PATENT DOCUMENTS 3,480,456 A * 11/1969 Forkner ............... A01C 1/06
                                                              241/23
3,655,838 A    4/1972 Price et al.
(Continued)

FOREIGN PATENT DOCUMENTS

WO    2011018504 A2    2/2011
WO    2015058173 A1    4/2015

OTHER PUBLICATIONS

Written Opinion of the International Searching Authority—PCT/US2016/56322, filed Oct. 11, 2016—dated Dec. 28, 2016.
(Continued)

*Primary Examiner* — Blessing M Fubara
(74) *Attorney, Agent, or Firm* — Eric A. Meade; John C. Todaro

(57) ABSTRACT

The present invention provides a process for preparing enterically-coated lyospheres comprising a therapeutic agent comprising: a.) providing lyospheres comprising the therapeutic agent; b.) coating said lyospheres with an enteric polymer coating composition; and c.) isolating said enterically-coated lyospheres. In other embodiments, the invention provides dosage forms comprising a lyosphere comprising an effective amount of a therapeutic agent and an enteric polymer coating. In some embodiments, the therapeutic agent in the process or dosage form is a polypeptide, (Continued)

a protein, a peptide, a lipopeptide, a glycoprotein, a fusion protein, a protein conjugate, a cytokine, an enzyme, an antibody, an oligonucleotide, a vaccine vector, small molecule, a live virus, an inactivated virus, a virus-like particle, a viral protein subunit, an adjuvant, microbiome, a prebiotic, a probiotic, or an ectobiotic. In some embodiments of the present invention, after oral administration the dosage forms containing the enterically-coated lyospheres provide a method of delivering a therapeutic agent to the ileum, ileo-caecal junction, colon or a combination thereof in a subject.

22 Claims, 7 Drawing Sheets

Specification includes a Sequence Listing.

(56) References Cited

U.S. PATENT DOCUMENTS

| | | | |
|---|---|---|---|
| 3,767,790 A | 10/1973 | Guttag | |
| 3,860,490 A | 1/1975 | Guttag | |
| 4,377,568 A | 3/1983 | Chopra | |
| 4,397,844 A | 8/1983 | Baschang et al. | |
| 5,597,562 A | 1/1997 | Nomura et al. | |
| 5,656,597 A * | 8/1997 | Skrabanja | A61K 9/1694 424/491 |
| 5,824,339 A | 10/1998 | Shimizu et al. | |
| 6,106,836 A * | 8/2000 | Wilderbeek | A61K 9/1694 424/1.11 |
| 6,139,875 A | 10/2000 | Adams et al. | |
| 8,535,640 B1 | 9/2013 | Sung et al. | |
| 9,119,794 B2 | 9/2015 | Middelbeek et al. | |
| 2010/0003331 A1* | 1/2010 | Ahmed | A61K 9/0004 424/489 |
| 2010/0136125 A1 | 6/2010 | Jacobus et al. | |
| 2010/0210004 A1* | 8/2010 | Kappe | A61K 39/015 435/258.2 |
| 2010/0260796 A1 | 10/2010 | Belin-Poput | |
| 2010/0291092 A1* | 11/2010 | Kozel | G01N 33/56911 424/139.1 |
| 2011/0117196 A1* | 5/2011 | Gordon | A61K 9/205 424/485 |
| 2012/0049412 A1 | 3/2012 | Middlebook et al. | |
| 2014/0017318 A1 | 1/2014 | O'Connell et al. | |
| 2014/0294872 A1 | 10/2014 | Barr et al. | |

OTHER PUBLICATIONS

Cole, E.T., et al, "Enteric Coated PMC Capsules Designed to Achieve Intestinal Targeting", International Journal Pharmaceutics, 2002, pp. 83-95, 231.

Fang, Yu., et al, "EEudragit L/HPMCAS Blend Enteric-Coated Lansoprazole Pellets: Enhanced Drug Stability and Oral Bioavailability", AAPS Pharm. Sci. Tech, 2014, pp. 513-521, vol. 15, No. 3.

Kiew, Tie Ti, et al, "Preserving the Supersaturation Generation Capability of Amorphous Drug-Polysaccharide Nanoparticle Complex After Freeze Drying", International Journal of Pharmaceutics, 2015, pp. 115-123.

Mercier, G.T., et al, "Oral Immunization of Rhesus Macaques With Adenoviral HIV Vaccines Using Enteric-Coated Capsules", Vaccine, 2007, pp. 8687-8701, vol. 25.

Tirpude, R.N., et al, "Rabeprazole Sodium Dlayed-Release Multiparticlates: Effect of Enteric Coating Layers on Product Performance", Journal of Advanced Pharmaceutical Technology & Research, 2011, pp. 184-191, Vo. 2, No. 3.

EP Search Report, 168560118, dated May 17, 2019.

* cited by examiner

FIG.7

PROCESS FOR PREPARING FORMULATIONS FOR GASTROINTESTINAL-TARGETED THERAPIES

CROSS REFERENCE TO RELATED APPLICATIONS

This application is a U.S. National Phase application under 35 U.S.C. § 371 of PCT Application No. PCT/US2016/056322, filed Oct. 11, 2016, which claims priority under 35 U.S.C. § 119(e) from provisional Application No. 62/242,718, filed Oct. 16, 2015.

FIELD OF THE INVENTION

The present invention relates to processes for preparing pharmaceutical formulations useful for delivering therapeutic agents to specific regions of the gastrointestinal tract, e.g., the small intestine or colon, following oral administration of the formulations to a subject.

BACKGROUND OF THE INVENTION

Identification of any publication in this section or any section of this application is not an admission that such publication is prior art to the present invention.

Considerable interest exists in the development of pharmaceutical formulations which are capable of selective delivery of drugs into the colon and other sites within the gastrointestinal tract. Site specific delivery to the colon provides certain advantages for the development of pharmaceutical products. Delivery of therapeutic agents specifically to the colon allows treatment of diseases and disorders that primarily affect the colon. Colonic disorders which may benefit from selective delivery of drug include, but are not limited to, intestinal bowel diseases such as Crohn's disease and ulcerative colitis, irritable bowel syndrome, spastic colon, C. difficile infection, constipation and colon cancer.

The ability to deliver such compounds to the gastrointestinal tract using an orally administered formulation provides for more convenient administration and better patient compliance. Furthermore, localized delivery of therapeutic agents to the gastrointestinal tract via the oral route may lead to improved efficacy of the agent while reducing the side effects associated with parenteral administration of such a compound. The colon is often identified as a preferred delivery site because of slow transit, its small volume and a lack of vigorous stirring within it, leading to an ability to create local conditions favorable to stabilization of the drug. The colon also lacks certain digestive enzymes (proteases) that can affect adversely drug stability.

Several approaches for site-specific delivery to the gastrointestinal tract have been employed including time release, pH-responsive or microbial-trigger approaches. Delivery systems that use time-based release mechanisms take into consideration the typical gastrointestinal transit time in humans, and seek to release of the drug in the small and large intestine. Microbial trigger drug delivery systems take advantage of the colonic microbiota to digest polymer coatings in the colon while resisting digestion in the small intestine. Delivery systems based on a pH responsive mechanism are designed to trigger drug release based on the pH associated with different regions of the intestinal tract to target drug delivery at specific sites in the intestine.

Site-specific delivery into the small intestine has been achieved for many years by the use of pH-sensitive (enteric) coatings. By optimizing the formulation, in particular, the type of polymer, delivery to specific target sites with the gastrointestinal tract can be achieved. While this approach has been successful in providing enteric dosage forms for delivering small molecule therapeutic agents, use of this approach for delivering biological macromolecular therapeutic agents such as proteins has been less successful due to the sensitivity of such agents to the formulation and processing methods used to prepare such enteric formulations.

Various attempts to overcome the sensitivity problems associated with biological macromolecular therapeutic agents (e.g., proteinaceous agents) have been proposed which include initial preparation of lyophilates. For instance, U.S. Pat. No. 5,597,562 discloses pharmaceutical preparations that are stated to allow absorption of granulocyte colony stimulating factor and erythropoietin from the gastrointestinal tract. The patent discloses that the drug preparations are prepared by lyophilizing a solution containing the protein, a fatty acid, an optional excipient, in a buffer solution to form a powder. The powder is used either to fill a capsule or formed into granules, which are then enterically coated.

Similarly, U.S. Pat. Nos. 3,860,490 and 3,767,790 disclose the entrapment of influenza vaccine in hydrophilic polyacrylates or polymethacrylates to provide controlled release formulations. U.S. Pat. No. 4,397,844 discloses the formation of chemical derivatives of antigens, including derivatives of influenza vaccine, which are said to produce an increase in immunoresponse and which are formulated with solid excipients to make tablets or tablet cores. EP-A 86/06635 discloses a complex of an immunogen to interact with the mucosal ephithelium upon oral administration. Mercier, G. T et al. in *Oral Immunization of Rhesus Macaques with Adenoviral HIV Vaccines Using Enteric-Coated Capsules*, Vaccine 25, pp 8687-8701 (2007) discloses enterically coated hydroxypropylmethyl cellulose capsules containing lyophilized adenoviral vectors.

Several drawbacks are associated with use of conventional lyophilized bulk powder approach which are filled into capsules or compressed into tablets that are enterically coated for targeting the unitary dosage form (capsule/tablet) to the intestinal tract. The lyophilized bulk powder is often fluffy and is associated with poor bulk density that results in inadequate powder flow. In order to improve the powder flow, the lyophilized bulk is often blended with flow enhancers such as glidants along with other commonly used pharmaceutical excipients such as lubricants, disintegrants, and fillers. If the powder blend fails to have adequate flow properties, then inconsistent loading of the dose during subsequent downstream processing such as capsule filling or tablet compression will result in poor dose uniformity in the final dosage form. Furthermore, macromolecules such as proteins destabilize more readily compared to small molecules during blending with excipients due to chemical instability with the excipients. In addition, the macromolecule is subject to degradation due to the physical stress induced on the macromolecule during tablet compression processes or in the tamping processes used to fill capsules.

Furthermore, in the process of enterically coating the capsules, softening of the gelatin shell may occur during the coating step. The polymeric film may also insufficiently adhere to the capsule during the coating step, in particular, when using coating with organic solvents, resulting in peeling and splintering of the capsule. Other drawbacks resulting from the coating step include powder leakage from capsule caused by separation of the capsule body and cap.

Insufficient capsule integrity may also result in cracking of the polymeric film during the drying step of the enteric coating process.

While lyophilates have been used to prepare biological materials for storage and further processing into suitable dosage forms, another technique for preparing such materials involves preparing lyospheres. U.S. Pat. No. 3,655,838 discloses a process for separate freeze-drying of the various solutions comprising the various biological materials for a diagnostic test. Briefly, this process includes bringing droplets of each solution in direct contact with liquid nitrogen resulting in instantaneous freezing. The frozen droplets are transferred to a freeze-dryer and are subsequently dried. The resulting dry spheres are called lyospheres. The first lyospheres owed their form and name to the fact that they were frozen as spherical droplets and subjected to lyophilisation afterwards. Small volumes of fluid in any possible form can also be frozen by contacting them with cold surfaces, e.g., by adding some fluid to small holes in a cold heat-conducting surface, followed by lyophilisation.

U.S. Pat. No. 9,119,794 also discloses a process for forming a lyosphere which is in the form of a tablet. Such processes are disclosed to be able to result in fast-disintegrating tablets containing a medicinal substance which are suitable for oral use.

U.S. Patent Application Publication No. US2014/0294872 discloses a process for preparing lyophilized pellets of biological materials. The pellets are said to have a substantially spherical shape, and are prepared by freezing droplets of a liquid composition of a desired biological material on a flat, solid surface, in particular, a surface that does not have any cavities, followed by lyophilizing the frozen droplets. These processes are stated to be useful for preparing lyophilized pellets having a high concentration of a desired biological material, in particular a therapeutic protein or vaccine, and which have a faster reconstitution time than lyophilized powder cakes prepared in vials.

New processes for preparing enterically-coated dosage forms that are, in particular, suitable for macromolecular therapeutic agents are desirable. New dosage forms that specifically deliver therapeutic agents to the ileum, ileo-caecal junction, colon or a combination thereof in patients provide health care practitioners with additional options to treat diseases or disorders. For instance, in the therapy of certain disorders such as an irritable bowel disease or *C. difficile* infection, delivering a therapeutic agent to such sections of the gastrointestinal tract is particularly desirable.

The present invention provides such processes, dosage forms and delivery methods.

SUMMARY OF THE INVENTION

In one aspect, the present invention provides a process for preparing enterically-coated lyospheres comprising a therapeutic agent comprising:
 a.) providing lyospheres comprising the therapeutic agent;
 b.) coating said lyospheres with an enteric polymer coating composition; and
 c.) isolating said enterically-coated lyospheres.

In another aspect, the present invention provides a dosage form comprising a lyosphere comprising an effective amount of a therapeutic agent and an enteric polymer coating.

In yet another aspect, the present invention provides a dosage form comprising:
 a first lyosphere containing a therapeutic agent and a first enteric coating; and
 a second lyosphere containing said therapeutic agent and a second enteric coating.

In another aspect, the present invention provides a dosage form comprising:
 a first lyosphere containing a first therapeutic agent and a first enteric coating and
 a second lyosphere containing a second therapeutic agent and a second enteric coating.

In still another aspect, the present invention provides a dosage form comprising a coated lyosphere comprising a therapeutic agent coated with a pH-independent polymeric coating and an enteric polymeric coating overlaying the pH-independent polymeric coating.

In another aspect, the invention provides a method of treating a disease or disorder, comprising administering a dosage form containing a lyosphere comprising a therapeutic agent, wherein the lyosphere contains an enteric coating to a subject in need thereof.

In yet another aspect, the present invention provides a method of delivering a therapeutic agent to the jejunum, ileum, ileo-caecal junction, colon or a combination thereof in a subject, comprising administering a dosage form containing a lyosphere containing an effective amount of a therapeutic agent, wherein the lyosphere contains an enteric coating to said patient.

BRIEF DESCRIPTION OF THE DRAWINGS

FIG. 7 shows the recovery of secondary structure of anti-hPD1 mAb from enterically coated lyospheres (with 61.4% weight gain) as measured by circular dichroism following dissolution in 10 mM phosphate buffered saline, pH 7.4 in comparison with uncoated anti-hPD1 mAb.

DETAILED DESCRIPTION OF THE INVENTION

The present invention provides a process for preparing enterically-coated lyospheres comprising a therapeutic agent, enterically coated lyospheres prepared using the process, and uses thereof.

The applicants have discovered processes for preparing enterically coated lyospheres that result in dosage forms that allow targeted delivery of therapeutic agents to various regions of the gastrointestinal tract. The processes of the present invention also include preparing lyospheres which are sufficiently robust to withstand the coating steps, but which also release the therapeutically active agent upon dissolution of the enteric coating to the desired regions in the gastrointestinal tract.

Using enterically-coated lyospheres as dosage to target specific regions of the gastrointestinal tract provide a number of advantageous properties as compared with using coated dosage forms containing powder lyophilates. Lyospheres are comparatively denser as compared to powder lyophilates. In contrast to lyophilized powders, lyospheres do not typically require a blending step to achieve acceptable flow properties. Since the lyospheres formed by the process of their invention are themselves enterically coated, the lyospheres can be directly filled into a capsule or sachet thereby eliminating the need for coating the capsule. Furthermore, the particulate nature of enterically-coated lyospheres allows flexibility to accommodate these into capsules, sachets or bottles. In some embodiments, high drug loading can be achieved using enterically-coated lyospheres as compared with powdered lyophilates where drug loading is limited by the volume of the final dosage form, e.g., the capsule.

The processes of the present invention also allow preparation of fixed dosage forms combining two or more therapeutic agents since the processes allow separate coating of two separate populations of lyospheres containing distinct therapeutic agents which can then be combined together in the final dosage form e.g., a capsule or sachet. The selection of the polymer and the coating thickness on discrete populations of lyospheres can be manipulated to tailor different release profiles and target different regions in the gastrointestinal tract for each population of lyosphere.

Furthermore, preparing lyospheres can reduce the cost of manufacture and improve the shelf-life of certain therapeutic agents as compared preparing dosage forms containing lyophilates in a conventional manner. Conventional lyophilized cakes containing a therapeutic agent (e.g., a biological macromolecule) are generally prepared by aliquoting a desired amount of the agent, which is typically present in a buffered solution with appropriate stabilizers into a glass container. The glass container is then subjected to cooling, freezing, annealing, primary drying and secondary drying steps. Such vial lyophilization is a heat and mass-transfer limited process, and such a limitation significantly slows down the sublimination drying process at solute concentrations >15% w/w. In contrast, preparing lyospheres from compositions having a high solute concentration, e.g., concentrations above 20%, is possible due to a high surface/volume ratio of the composition. Such compositions may have high concentrations of sugars and other stabilizers, e.g., sucrose, trehalose, sucrose/trehalose mixtures, mannitol, dextrose, dextran and mixtures of such sugars and may result in improved thermostability of biological macromolecular agents, which are often susceptible to degradation under conditions used to prepare conventional lyophilates. The high concentration of stabilizers in the lyosphere provides biological macromolecular agents with added stability in the finalized dosage form, and thereby contributes to the shelf-life of the final dosage form.

I. Definitions and Abbreviations

So that the invention may be more readily understood, certain technical and scientific terms are specifically defined below. Unless specifically defined elsewhere in this document, all other technical and scientific terms used herein have the meaning that would be commonly understood by one of ordinary skill in the art to which this invention belongs when used in similar contexts as used herein.

As used herein, including the appended claims, the singular forms of words such as “a,” “an,” and “the,” include their corresponding plural references unless the context clearly dictates otherwise.

“About” when used to modify a numerically defined parameter, e.g., the dosage for a therapeutic agent discussed herein, or the length of treatment time, means that the parameter may vary by as much as 10% above or below the stated numerical value for that parameter.

“Consists essentially of” and variations such as “consist essentially of” or “consisting essentially of” as used throughout the specification and claims, indicate the inclusion of any recited elements or group of elements, and the optional inclusion of other elements, of similar or different nature than the recited elements, which do not materially change the basic or novel properties of the specified dosage regimen, method, or composition.

“Individual” or “animal” or “patient” or “mammal” or “subject” is meant any subject, particularly a mammalian subject, for whom any of the claimed compositions and methods is needed or may be beneficial. In preferred embodiments, the subject is a human. In more preferred embodiments, the subject is an adult human, i.e., at least 18 years of age.

“Isolated” is typically used to reflect the purification status of a biological molecule such as RNA, DNA, oligonucleotide, or protein, and in such context means the molecule is substantially free of other biological molecules such as nucleic acids, proteins, lipids, carbohydrates, or other material such as cellular debris and growth media. Generally, the term “isolated” is not intended to refer to a complete absence of other biological molecules or material or to an absence of water, buffers, or salts, unless they are present in amounts that substantially interfere with the methods of the present invention.

“Lyosphere,” as used herein, refers to dried unitary bodies comprising therapeutically active agents (or in the case of vaccines, adjuvants) which are formed from a frozen mass of a predetermined shape which can be, for example, substantially spherical or ovoid-shape, which when dried retain sufficient robustness to withstand further processing including coating and packaging steps. In some embodiments, the lyosphere diameter is from about 2 to about 12 mm, preferably from 2 to 8 mm, such as from 2.5 to 6 mm or 2.5 to 5 mm. In some embodiments, the volume of the lyosphere is from about 20 to 100 μL, preferably from 20 to 100 μL, such as from 20 to 50 μL. In embodiments wherein the lyosphere is not substantially spherical, the size of the lyosphere can be described with respect to its aspect ratio, which is the ratio of the longer dimension to the shorter dimension. The aspect ratio of the lyospheres can be from 0.5 to 2.5, preferably from 0.75 to 2, such as from 1 to 1.5.

Figure 1A:
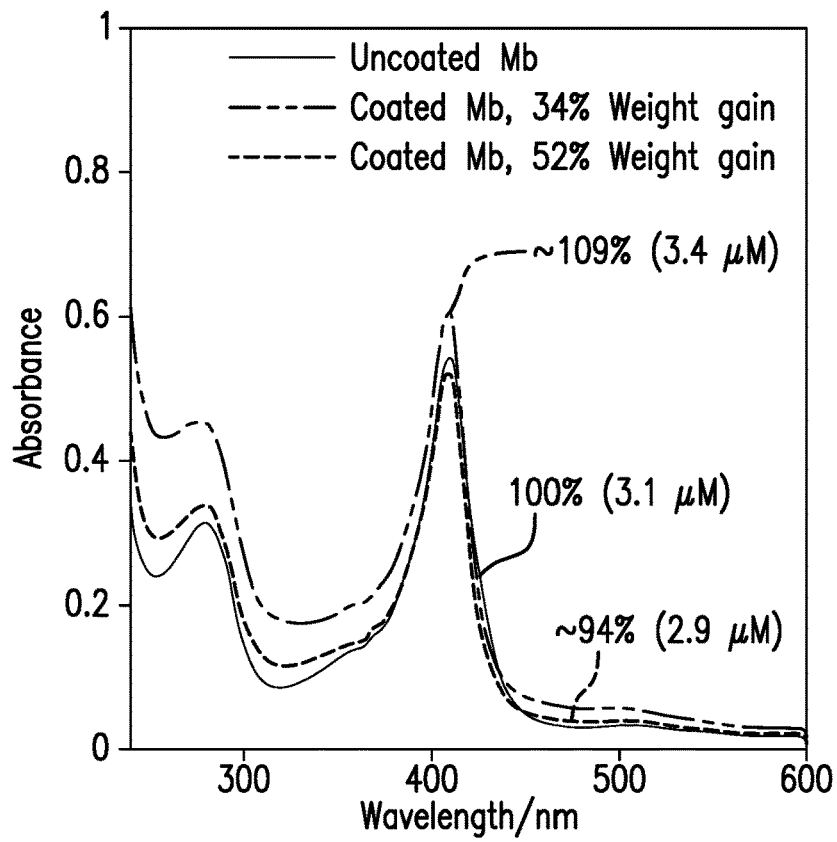
FIG. 1A shows the yield recovery of myoglobin from enterically-coated lyospheres as measured by UV-Vis spectroscopy at λ 410 nm, following dissolution in 10 mM phosphate buffered saline, pH 7.4 in comparison with uncoated myoglobin.

"Pharmaceutically acceptable" refers to molecular entities and compositions that are "generally regarded as safe"— e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

A "pH-independent polymeric coating" refers to a polymeric coating wherein the dissolution profile is independent of the intestinal pH. Examples of pH-independent polymeric coatings include ethylcellulose with hydroxypropylmethyl cellulose or hydroxypropyl cellulose as a pore former (e.g., Aquarius® coating system from Ashland; Surelease® coating systems from Colorcon); polyvinyl acetate based polymers (such as Kollicoat SR®/Kollicoat SR30D® alone in combination with Kollicoat IR® from BASF) or poly(ethyl acrylate-co-methyl methacrylate-co-trimethylammonioethyl methacrylate chloride) 1:2:0.2 or poly(ethyl acrylate-co-methyl methacrylate-co-trimethylammonioethyl methacrylate chloride) 1:2:0.1 (such as Eudragit RL®, RS® or combinations thereof from Evonik).

"Sugar" refers to any of a group of water-soluble carbohydrates of relatively low molecular weight. The term sugar includes reducing sugars (such as fructose and maltose), non-reducing sugars (such as sucrose and trehalose), sugar alcohols (such as xylitol and sorbitol) and sugar acids (such as gluconic acid and tartaric acid).

"Treat" or "treating" means to administer a therapeutic agent, such as a composition containing the therapeutic agents described herein, internally or externally to an individual in need of the therapeutic agent. Individuals in need of the agent include individuals who have been diagnosed as having, or at risk of developing, a condition or disorder susceptible to treatment with the agent, as well as individuals who have, or are at risk of developing, one or more adverse effects of treatment with a first therapeutic agent that are susceptible to alleviation with a second therapeutic agent. Typically, the therapeutic agent is administered in a therapeutically effective amount, which means an amount effective to produce one or more beneficial results. The therapeutically effective amount of a particular agent may vary according to factors such as the disease state, age, and weight of the patient being treated, and the sensitivity of the patient, e.g., ability to respond, to the therapeutic agent. "Treat" or "treating" includes preventing the development of occurrence of a condition, disease, or disorder in a subject.

The following reagents and units of measurements may be referred to by their abbreviations:

FaSSIF=fasted Simulated small intestinal fluid
h=hour
kg=kilograms
mTorr=millitorrs
min=minutes
Mb=myoglobin
mg=milligrams
mL=milliliters
mm=millimeters
mM=millimolar
SCoF=simulated colonic fluid
SGF=simulated gastric fluid
μL=microliters

II. Embodiments of the Invention

In a first aspect, the present invention provides a process for preparing enterically-coated lyospheres comprising a therapeutic agent.

In embodiment no. 1, the present invention provides the process for preparing enterically-coated lyospheres comprising a therapeutic agent comprising:
 a.) providing lyospheres comprising the therapeutic agent;
 b.) coating said lyospheres with an enteric polymer coating composition; and
 c.) isolating said enterically-coated lyospheres.

In embodiment no. 2, the present invention provides a process as set forth in embodiment no. 1 wherein in step b.) the enteric polymer coating composition comprises an anionic polymer selected from an acrylic or methacrylic acid copolymer, a carboxylic acid-containing cellulosic polymer, a carboxylic acid-containing polyvinyl acetate copolymer, or shellac.

In embodiment no. 3, the present invention provides a process as set forth in embodiment no. 2, wherein
 the acrylic or methacrylic acid copolymer is poly(methacrylic acid, methyl methacrylate) 1:1, poly(methacrylic acid, methyl methacrylate) 1:2, poly(methacrylic acid, ethyl acrylate) 1:1; or poly(methyl acrylate, methyl methacrylate, methacrylic acid) 7:3:1
 the carboxylic acid-containing cellulosic polymer is hydroxypropylmethyl cellulose phthalate, cellulose acetate phthalate (CAP), cellulose acetate trimellitate, hydroxypropylmethyl cellulose succinate; and
 the carboxylic acid-containing polyvinyl acetate copolymer is polyvinyl acetate phthalate.

In embodiment no. 4, the present invention provides a process as set forth in any one of embodiment nos. 1-3, wherein step b.) comprises spray or dip coating the lyospheres with the enteric polymer coating composition.

In embodiment no. 5, the present invention provides a process as set forth in embodiment no. 4, wherein said coating step b.) comprises spray-coating the lyospheres with the enteric polymer coating composition.

In embodiment no. 6, the present invention provides a process as set forth in embodiment no. 5, wherein said spray-coating is bottom spray-coating, tangential spray-coating, or pan-coating. Preferably said spray-coating is bottom spray-coating. Spray-coating can be performed using a Wurster column set-up, or in the absence of a Wurster column wherein the lyospheres move around a central rotating cone.

In embodiment no. 7, the present invention provides a process as set forth in any one of embodiment nos. 1-6, wherein said enteric polymer coating composition is dispersed in an aqueous medium or an organic solvent, such as acetone or isopropanol. In embodiment no. 8, said enteric polymer coating composition is dispersed in an aqueous medium.

In embodiment no. 9, the present invention provides a process as set forth in any one of embodiment nos. 1-8, wherein the coating and isolating steps result in enterically-coated lyospheres having a weight gain of at least 10 wt. %, typically 10 to 200 wt. % as compared to the uncoated lyospheres. In embodiment no. 10, the weight gain is from 30 to 150 wt. %, such as from 60 to 110 wt. % or from 80 to 100 wt. %.

In embodiment no. 11, the present invention provides a process as set forth in any one of embodiment nos. 1-10, wherein the enteric polymer coating composition further comprises a plasticizer, a detackifier, or a surfactant.

In embodiment no. 12, the present invention provides a process as set forth in embodiment no. 1, wherein the process further comprises coating the lyospheres with a pH-independent polymer coating composition prior to coating the lyospheres with the enteric polymer coating composition.

In embodiment no. 13, the present invention provides a process as set forth in any one of embodiment nos. 1-12, wherein said lyospheres in step a.) are prepared by:

mixing the therapeutic agent, a sugar and a binding-gel forming agent in an aqueous medium to form an aqueous medium mixture;

segregating the aqueous medium mixture into unitary volumes;

freezing said unitary volumes to form unitary forms; and separating water from said unitary forms to yield the lyospheres.

In embodiment no. 14, the present invention provides a process as set forth in embodiment no. 13, wherein said separating comprises drying the unitary forms under conduction- or radiant-dominant drying to yield said lyospheres.

In embodiment no. 15, the present invention provides a process as set forth in any one of embodiment nos. 13 and 14, wherein said segregating, freezing, and separating steps comprise:

segregating the aqueous medium mixture into unitary volumes on a pre-cooled flat surface of a solid element to form the unitary forms;

removing the unitary forms from the flat surface, and drying the unitary forms under conduction- or radiant-dominant drying to yield said lyospheres.

In embodiment no. 16, the present invention provides a process as set forth in embodiment no. 13, wherein said separating comprises drying the unitary forms under a vacuum to yield said lyospheres.

In embodiment no. 17, the present invention provides a process as set forth in embodiment no. 13, wherein said segregating, freezing, and separating steps comprise:

filling cavities of a solid element with the aqueous medium mixture;

freezing the aqueous medium mixture while present in the cavities by extracting heat from the aqueous medium mixture through a cavity wall by conduction to form the unitary forms;

removing the unitary forms from the cavity, and drying the unitary forms in a vacuum to obtain the lyospheres.

In embodiment no. 18, the present invention provides a process as set forth in any one of embodiment nos. 13-17, wherein said binding-gel forming agent is a cellulosic polymer, polyvinylpyrollidone, starch, gelatin, polyethylene glycol, wax, a natural gum, a synthetic gum, or a combination thereof. In specific embodiments, the binding-gel forming agent is corn starch, pregelatinized starch, gelatin; polyethylene glycol, a wax; acacia sodium alginate, polyvinylpyrrolidone, hydroxypropyl cellulose (e.g., Nisso HPC-L, HPC-SL, HPC-SSL), hydroxypropylmethyl cellulose, methyl cellulose (e.g., Metolose SM-4), microcrystalline cellulose, ethyl cellulose, and hydroxyethyl cellulose.

In embodiment no. 19, the present invention provides a process as set forth in embodiment no. 18, wherein said binding-gel forming agent is a cellulosic polymer selected from hydropropylmethyl cellulose, hydroxypropyl cellulose, methyl cellulose, microcrystalline cellulose, ethyl cellulose, or a combination thereof.

In embodiment no. 20, the present invention provides a process as set forth in embodiment no. 18, wherein said binding-gel forming agent is hydroxypropylmethyl cellulose, which can selected from various viscosity grades of HPMC (e.g., Pharmatose® 603, 645, 606, 615, 904 (3-15 cP) from Shin-etsu; Metolose® (SM, 60SH; 65SH; 90SH) from Shin-etsu; Methocel® E5LV; E15LV from Colorcon. The hydroxypropylmethyl cellulose preferably has a viscosity from 2 to 15 centipoise (cp), preferably from 2 to 10 cp, such as from 2 to 6 cp.

In embodiment no. 21, the present invention provides a process as set forth in any one of embodiment nos. 13-20, wherein said binding-gel forming agent comprises from about 1 to 50% w/v of the aqueous medium mixture, for instance, from 2 to 40% w/v, from 3 to 30% w/v, from 4 to 20% w/v, from 5 to 15% w/v, or 7 to 10%/o w/v.

In embodiment no. 22, the present invention provides a process as set forth in any one of embodiment nos. 13-21, wherein said sugar is trehalose, sucrose, glucose, galactose, maltose, lactose, raffinose, fructose, saccharose, mannitol, sorbitol, xylitol, or a combination thereof.

In embodiment no. 23, the present invention provides a process as set forth in embodiment no. 22, wherein said sugar is trehalose.

In embodiment no. 24, the present invention provides a process as set forth in embodiment no. 22, wherein said sugar is a combination of trehalose and mannitol. In some embodiments, the trehalose and mannitol are present in the aqueous medium mixture at a ratio (weight ratio) of about 70:30, 60:40, 50:50 or 40:60.

In embodiment no. 25, the present invention provides a process as set forth in any one of embodiment nos. 22-24, wherein said aqueous medium mixture comprises from 5 to 50% w/v of the sugar. Preferably, the aqueous medium mixture comprises from 5 to 30% w/v of sugar, for example from 7 to 25% w/v, from 15 to 30% w/v, or from 15 to 25% w/v.

In embodiment no. 26, the present invention provides a process as set forth in any one of embodiment nos. 13-17, wherein the binding-gel forming agent is hydroxypropylmethyl cellulose and the sugar is trehalose.

In embodiment no. 27, the present invention provides a process as set forth in embodiment no. 26, wherein the ratio (weight ratio) of trehalose to hydroxypropylmethyl cellulose is from 10:1 to 1:5, such as ratios from 10:1 to 1.5:1 or from 4:1 to 2:1.

In embodiment no. 28, the present invention provides a process as set forth in any one of embodiment nos. 13-27, wherein said aqueous medium mixture is blended in the absence of gelatin.

In a second aspect, the present invention provides a dosage form comprising an enterically-coated lyosphere and a therapeutic agent.

In embodiment no. 29, the dosage form comprises an enterically-coated lyosphere prepared by the process of any one of embodiment nos. 1-28.

In embodiment no. 30, the present invention provides a dosage form comprising a lyosphere comprising a therapeutic agent and an enteric polymer coating, wherein the dosage form comprises an effective amount of the therapeutic agent.

In embodiment no. 31, the present invention provides the dosage form as set forth in embodiment no. 30, wherein the lyosphere further comprises a sugar and a binding-gel forming agent. In embodiment no. 32, the binding-gel forming agent is as set forth in embodiment no. 18 and the sugar is as set forth in embodiment no. 22. In embodiment no. 33, the binding-gel forming agent is as set forth in embodiment no. 20 and the sugar is as set forth in embodiment no. 24.

In embodiment no. 34, the present invention provides the dosage form as set forth in any one of embodiment nos. 31-33, wherein the sugar comprises 20 to 90/o w/w, and the binding-gel forming agent is 10 to 80% w/w based on the total weight of lyosphere in the absence of the enteric polymer coating.

In embodiment no. 35, the present invention provides the dosage form as set forth in any one of embodiment nos. 31-33, wherein the sugar comprises 35 to 85% w/w, and the binding-gel forming agent is 15 to 65% w/w based on the total weight of lyosphere in the absence of the enteric polymer coating.

In embodiment no. 36, the present invention provides the dosage form as set forth in any one of embodiment nos. 31-33, wherein the sugar comprises 45 to 75% w/w, and the binding-gel forming agent is 25 to 55% w/w based on the total weight of lyosphere in the absence of the enteric polymer coating.

In embodiment no. 37, the present invention provides a dosage form comprising:
a first lyosphere containing a therapeutic agent and a first enteric coating; and
a second lyosphere containing said therapeutic agent and a second enteric coating.

In embodiment no. 38, the present invention provides the dosage form as set forth in embodiment no. 37, wherein the first and second enteric coatings comprise the same enteric polymer.

In embodiment no. 39, the present invention provides the dosage form as set forth in embodiment no. 38, wherein the second lyosphere contains from 10 to 200% by weight more enteric coating than contained on the first lyosphere. For example, the second lyosphere can contain from 30 to 150%, 40-120%, or 80 to 100% more enteric coating than contained on the first lyosphere.

In embodiment no. 40, the present invention provides the dosage form as set forth in embodiment no. 37, wherein the second enteric coating is soluble at a pH higher than the first enteric coating.

In embodiment no. 41, the present invention provides the dosage form as set forth in embodiment no. 40, wherein the second enteric coating is soluble at a pH at or above 6.8 and the first enteric coating is soluble at a pH above 5.

In embodiment no. 42, the present invention provides a dosage form comprising: a first lyosphere containing a first therapeutic agent and a first enteric coating, and
a second lyosphere containing a second therapeutic agent and a second enteric coating.

In embodiment no. 43, the present invention provides the dosage form as set forth in embodiment no. 42, wherein the first and second enteric coatings comprise the same enteric polymer. In embodiment no. 44, the first and second enteric coatings comprise the same enteric polymer with the same coating weight gain.

In embodiment no. 45, the present invention provides the dosage form as set forth in embodiment no. 43, wherein the second lyosphere contains from 10 to 200% by weight more enteric coating than the first lyosphere. For example, the second lyosphere can contain from 30 to 150%, 40-120%, or 80 to 100% more enteric coating than the first lyosphere.

In embodiment no. 46, the present invention provides the dosage form as set forth in embodiment no. 42, wherein:
the first lyosphere further comprises a first sugar and first binding-gel forming agent;
the second lyosphere further comprises a second sugar and second binding-gel forming agent; and
wherein at least one of the following conditions apply:
the first sugar and the second sugars are different; or
the first binding-gel forming agent and second binding-gel forming agents are different.

In embodiment no. 47, the present invention provides a dosage form comprising a coated lyosphere comprising a therapeutic agent coated with a pH-independent polymeric coating and an enteric polymeric coating overlaying the pH-independent polymeric coating.

In embodiment no. 48, the present invention provides the dosage form as set forth in embodiment no. 47, wherein the coated lyosphere further comprises a barrier polymeric coating between the pH-independent polymeric and the enteric polymeric coatings. In such embodiment, the barrier polymeric coating overlays the pH-independent coating and the enteric polymeric coating overlays the barrier polymeric coating.

In embodiment no. 49, the present invention provides the dosage form of any one of embodiment nos. 29-48, wherein the dosage form is a capsule, tablet, or sachet.

In embodiment no. 50, the present invention provides the dosage form of any one of embodiment nos. 29-49, wherein the therapeutic agent comprises from 0.005 to 50 wt. % of the dosage form. Preferably the therapeutic agent comprises from 0.1 to 40 wt. % of the dosage form, such as from 0.5 to 30 wt. %, 1.0 to 20 wt. %, 2 to 15 wt. %, or 3 to 10 wt. % of the dosage form.

In embodiment no. 51, the present invention provides the dosage form of any one of embodiment nos. 29-49, wherein the therapeutic agent is present in the dosage form at from 0.01 to 500 mg. Preferably the therapeutic agent is present in the dosage form at from 0.05 to 400 mg, such as from 0.1 to 300 mg, 0.5 to 200 mg, 1 to 100 mg, 2 to 50 mg, or 3 to 25 mg.

In a third aspect, the present invention provides a method of treating a disease or disorder, comprising administering a dosage form containing an enterically-coated lyosphere comprising effective amount of a therapeutic agent to a subject in need thereof.

In embodiment no. 52, the method is for treating a disease or disorder, comprising administering a dosage form containing lyosphere comprising a therapeutic agent, wherein the lyosphere contains an enteric coat, to a subject in need of such treatment. The disease or disorder being treated can be, for example, a disease or disorder affecting the small intestine or large intestine. Such diseases or disorders include irritable bowel syndrome, celiac disease, diverticulitis, pouchitis, proctitis, mucositis, radiation-associated enteritis, short bowel disease, chronic diarrhea, gastroenteritis, duodenitis, jejunitis, peptic ulcer, Curling's ulcer, appendicitis, colitis, endometriosis, colorectal carcinoma, adenocarcinoma, inflammatory disorders such as diversion colitis, ischemic colitis, infectious colitis, chemical colitis, microscopic colitis (including collagenous colitis and lymphocytic colitis), atypical colitis, pseudomembraneous colitis, fulminant colitis, autistic enterocolitis, interdeminate colitis, jejunoiletis, ileitis, ileocolitis, granulomatous colitis, fibrosis, graft-versus-host disease, gastrointestinal graft-versus-host disease and infections affecting the GI tract such as *C. difficile*. In specific embodiments, the disease or disorder being treated is an inflammatory bowel disease or *C. difficile* infection.

In embodiment no. 53, the present invention provides a method of delivering a therapeutic agent to the jejunum, ileum, ileo-caecal junction, colon or a combination thereof in a subject, comprising administering a dosage form containing a lyosphere containing an effective amount of a therapeutic agent, wherein the lyosphere contains an enteric coating to said subject. In embodiment no. 54, the method of delivering is as set forth in embodiment no. 53, wherein the dosage form further contains an uncoated lyosphere containing a second therapeutic agent.

In embodiment no. 55, the present invention provides a method as set forth in any one of embodiment nos. 52-54, wherein the subject is a mammalian patient. In embodiment no. 56, the subject is a human.

In embodiment no. 57, the present invention provides a dosage form as set forth in any one of embodiment nos. 29-51 for use in therapy, such as therapy for any one of the diseases or disorder specified in embodiment no. 52. In embodiment no. 58, the present invention provides a dosage form as set forth in any one of embodiment nos. 29-51 for use in the manufacture of medicament.

In embodiment no. 59, the present invention provides the process, dosage form, method or use of any one of embodiment nos. 1-58, wherein the therapeutic agent which is a polypeptide, a protein, a peptide, a lipopeptide, a glycoprotein, a fusion protein, a protein conjugate, a cytokine, an enzyme, an antibody, an oligonucleotide, a vaccine vector, small molecule, a live virus, an inactivated virus, a virus-like particle, a viral protein subunit, an adjuvant, microbiome, a prebiotic, probiotic, or ectobiotic drug.

In embodiment no. 60, the present invention provides the process, dosage form, method, or use of embodiment no. 59, wherein the therapeutic agent has a molecular weight greater than 900 daltons.

III. Compositions of the Lyospheres Prior to Enteric Coating

The therapeutic agents that are contained within the enterically-coated lyospheres include a wide range of agents including both large molecules, which are often the products of biotechnological processes, or small molecule therapeutics having a molecular weight of less than 900 daltons. In some embodiments, the therapeutic agent is a polypeptide, a protein, a peptide, a lipopeptide, a glycoprotein, a fusion protein, a protein conjugate, a cytokine, an enzyme, an antibody, an oligonucleotide, a vaccine vector, small molecule, a live virus, an inactivated virus, a virus-like particle, a viral protein subunit, an adjuvant, or a microbiome (prebiotic, probiotic, or ecobiotic).

In certain embodiments, the therapeutic agent is a peptide or polypeptide (a long, continuous and unbranched peptide chain) containing 50 or fewer amino acid residues. Such peptides and polypeptides can be used for treating disorders or diseases affecting the gastrointestinal tract such as Crohn's disease, ulcerative colitis, and *C. difficile* infection. In specific embodiments, the peptide can be a derivative such as a lipopeptide (e.g., ramoplanin) or glycopeptide.

In certain embodiments, the therapeutic agent is a protein containing one or more long chains of amino acid residues such as monoclonal antibodies that can also be used for treating the diseases affecting the gastrointestinal tract. Examples of such antibodies include golimumab, infliximab, certolizumab, ustekinumab, adalimumab, and BI 655066.

In some embodiments, the monoclonal antibodies are directed to immune checkpoint blockage targets such as anti-CTLA4 (e.g., ipilimumab), anti-PD-1 receptor anti-programmed death-1 (e.g., nivolumab, pembrolizumab, tremelimumab, atezolizumab). In some embodiments, the therapeutic agents are antibodies targeting PD-LI, (e.g., BMS-936559, MPDL3280A, MEDI4736).

In other embodiments, the therapeutic agent is an oligonucleotide which is a short single stranded segment of DNA, RNA, (e.g., mRNA, sRNA) or hydrolytically stable derivatives thereof having 200 or fewer nucleic residues. Such oligonucleotides are typically complementary to a selected target sequence. Examples of such oligonucleotides include GED-0301, which is a synthetic single-stranded O,O-linked phosphorothioate oligonucleotide that binds the region 107-128 of the human Smad7 complementary DNA sequence.

In other embodiments, the therapeutic agent is a probiotic, ecobiotic or a combination thereof (e.g., SER-109 (a microbiome therapeutic for *C. difficile*), SER-155 (an ectobiotic microbiome therapeutic), SER-262 (an ectobiotic microbiome therapeutic), SER-287 (microbiome therapeutic for ulcerative colitis)) which can be useful in treating inflammatory bowel disease (e.g., ulcerative colitis, Crohn's disease, primary or recurrent *C. difficile* infections, post-Abx dysbiosis). For instance, such probiotics can include strains of *Clostridia* bacteria which may increase the number of regulatory T cells to result in an anti-inflammatory effect.

In some embodiments, the therapeutic agent is a small molecule. For instance, the therapeutic agent may be useful in treating inflammatory bowel disease such as azathioprine, mercaptopurine, and methotrexate.

In other embodiments, the therapeutic agent is a vaccine. For instance, the vaccine can be a replicating vaccine vector that could infect and replicate in the small or large intestine to generate the desired immune response. The vaccine may also be a non-replicating antigen, such as a protein, which can be taken up by Peyer's patches to generate a desired systemic immune response. In some embodiments, the vaccine is an enveloped virus selected from cytomegalovirus, herpes simplex virus, measles, mumps, rubella, respiratory syncytial virus, Epstein-Barr virus, rabies, Hepatitis B, Hepatitis C and varicella-Zoster virus. In other embodiments, the vaccine is a non-enveloped virus selected from adenovirus, parvovirus, polio virus, Norwalk virus and rotavirus.

In some embodiments, the vaccine is a virus-like particle (VLP). Such VLP vaccines include vaccines for Hepatitis B, Chikungunya and human papillomavirus.

In certain embodiments, the vaccine is a combination vaccine. Examples of combination vaccines of live viruses is MMR (measles, mumps and rubella) and PROQUAD (measles, mumps, rubella, and varicella).

In some embodiments, the vaccine antigen can be co-delivered with an adjuvant either in the same or in separate enterically-coated lyospheres.

The polypeptides, peptides, monoclonal antibodies, oligonucleotides, ectobiotics, probiotics, and vaccines which are incorporated in the processes of the present invention are typically provided in compositions which include additional excipients such as buffering agents (e.g., histidine buffer, surfactants) which stabilize these agents from degradation.

The inventors of the present invention have discovered specific compositions that result in lyospheres which have minimal bead attrition and which resist disintegration during the coating process. The compositions provided by the present invention also result in lyospheres which possess adequate flow characteristics which facilitate the coating process. In some embodiments, the therapeutic agent is mixed in aqueous medium containing a sugar and a binding-gel forming agent in an aqueous medium to form an aqueous medium mixture.

Inclusion of the sugar in the aqueous medium mixture stabilizes proteinaceous agents, and also results in an increased rigidity of the lyosphere. Examples of such sugars include trehalose, sucrose, glucose, galactose, maltose, lactose, raffinose, fructose, saccharose, mannitol, sorbitol, xylitol, or a combination thereof.

The binding-gel forming agent included in the aqueous medium mixture has a dual role of acting as a binder to increase the rigidity of the lyosphere material as well as being a gel former that prevents disintegration of the lyosphere during the coating process. The binding-gel forming agent may be a cellulosic polymer, polyvinylpyrollidone, starch, gelatin, polyethylene glycol, wax, a natural gum, a synthetic gum, or a combination thereof.

In aqueous medium mixtures containing proteinaceous agents, protease inhibitors may be included in the aqueous medium mixture to enhance the stability of the protein in the intestinal environment.

In some embodiments, the aqueous medium mixtures contain additional optional excipients including diluents, buffers, amino acids (e.g., glycine, glutamine, asparagine, arginine or lysine), chelating agents, surfactants, polyols, bulking agents, stabilizers, cryoprotectants, lyoprotectants, solubilizers, salts, tonicity agents (e.g., alkali metal halides, mannitol, sorbitol), delivery vehicles, and microbial preservatives.

IV. Polymeric Coating Compositions

The enteric polymer coating composition used in coating the lyosphere typically contains an anionic polymer selected from an acrylic or methacrylic acid copolymer, a carboxylic acid-containing cellulosic polymer, a carboxylic acid-containing polyvinyl acetate copolymer, or shellac.

In some embodiments, the acrylic or methacrylic acid copolymer is poly(methacrylic acid, methyl methacrylate) 1:1, poly(methacrylic acid, methyl methacrylate) 1:2, poly(methacrylic acid, ethyl acrylate) 1:1; or poly(methyl acrylate, methyl methacrylate, methacrylic acid) 7:3:1. In other embodiments, the carboxylic acid-containing cellulosic polymer is hydroxypropylmethyl cellulose phthalate, cellulose acetate phthalate (CAP), cellulose acetate trimellitate, hydroxypropylmethyl cellulose succinate. In yet other embodiments, the carboxylic acid-containing polyvinyl acetate copolymer is polyvinyl acetate phthalate.

Some of the polymethacrylate-based polymers set forth above are available as EUDRAGIT polymers from Evonik Industries, Germany. For example, EUDRAGIT FS 30 D is the aqueous dispersion of an anionic copolymer based on methyl acrylate, methyl methacrylate and methacrylic acid. It is insoluble in acidic media, but dissolves above pH 7.0. EUDRAGIT L30D-55 is an aqueous suspension of a poly(methacrylic acid-co-ethyl acrylate) 1:1 copolymer which dissolves above pH 5.5. EUDRAGIT S100 is a copolymer of methacrylic acid-methyl methacrylate (1:2) that dissolves above pH 7.0. EUDRAGIT L100 is a copolymer of methacrylic acid-methyl methacrylate (1:1) which dissolves above pH 6.0.

Preferred anionic polymer systems for targeting the colon include a mixture of EUDRAGIT FS 30 D/EUDRAGIT L30-D55 of 50:50 to 100:0% w/w. More preferred ratios are 60:40%, 70:30%, 80:20%, 85:15%, or 90:10%0 or 100% EUDRAGIT FS 30 D.

Another preferred polymer system for targeting the colon includes a mixture of EUDRAGIT S 100/EUDRAGIT L100 of 50:50 to 100:0% w/w, for example, 70:30%, 80:20%, 85:15%, or 90:10% or 100% EUDRAGIT S100.

In addition to the anionic polymer, the enteric polymer coating composition may further contain an a plasticizer, a detackifier, or a surfactant (e.g., Tween 20 or 80). Plasticizers includes triethyl citrate, stearic acid, tracetin, D-alpha-tocopheryl polyethyleneglycol succinate, and high molecular weight polyethylene glycol polymers such as PEG3350 from Sigma-Aldrich. Detackifiers or anti-tacking agents include talc, glyceryl monostearate, and magnesium stearate. Surfactants include sodium dodecyl sulfate, various grades of CREMOPHORs (BASF, Ludwigshafen, Germany), polysorbates (e.g., Tween 20, 40, or 80, SOLUTOL, SPANs), and polyethylene glycol.

In some embodiments, such additional additives for the enteric polymer coating compositions are available as aqueous suspensions containing an anti-tacking agent, a plasticizer and a surfactant. For instance, PLASACRYL from Evonik Industries, Germany can be included which contains a combination of these further additives.

The enterically-coated lyospheres may be optionally coated with an aqueous dispersion of fumed silica before they are filled into a capsule, sachet or bottle to prevent agglomeration of the lyospheres.

In some embodiments, the lyospheres may be coated with a pH-independent polymeric coating in addition to an enteric polymeric coating. Examples of pH-independent polymeric coatings include ethylcellulose with hydroxypropylmethyl cellulose or hydroxypropyl cellulose as a pore former (e.g., Aquarius® coating system from Ashland; Surelease® coating systems from Colorcon); polyvinyl acetate based polymers (such as Kollicoat SR®/Kollicoat SR30D® alone or in combination with Kollicoat IR® from BASF) or poly(ethyl acrylate-co-methyl methacrylate-co-trimethylammonioethyl methacrylate chloride) 1:2:0.2 or poly(ethyl acrylate-co-methyl methacrylate-co-trimethylammonioethyl methacrylate chloride) 1:2:0.1 (such as Eudragit RL®, RS® or combinations thereof from Evonik).

In specific embodiments of lyospheres containing pH-independent polymeric and enteric polymeric coatings, the lyosphere may include a barrier polymeric coating in addition to pH-independent polymeric and enteric polymeric coatings. Coating composition suitable for forming the barrier polymeric coating include low viscosity ethylcellulose coatings such as Surelease®, available from Colorcon, Harleysville, Pa.

V. Processes for Preparing the Uncoated Lyospheres

In some embodiments, the unitary volumes containing the aqueous medium mixture are formed on a solid element containing cavities. The solid element is cooled below the freezing temperature of the mixture, the cavities are filled with the mixture, and the mixture is solidified while present in the cavity to form the unitary forms. The unitary forms are dried in a vacuum to provide the lyospheres. U.S. Pat. No. 9,119,794, the disclosure of which is herein incorporated by reference, discloses similar processes for forming lyospheres.

In other embodiments, the lyospheres are formed in a substantially spherical shape and are prepared by freezing droplets of a liquid composition of a desired biological material on a flat, solid surface, in particular, a surface that does not have any cavities, followed by lyophilizing the unitary forms. U.S. Patent Application Publication No. US2014/0294872, the disclosure of which is herein incorporated by reference, discloses similar processes for forming lyospheres.

Briefly, in some embodiments the process comprises dispensing at least one liquid droplet having a substantially spherical shape onto a solid and flat surface (i.e., lacking any sample wells or cavity), freezing the droplet on the surface without contacting the droplet with a cryogenic substance and lyophilizing the frozen droplet to produce a dried pellet that is substantially spherical in shape. The process may be used in a high throughput mode to prepare multiple dried pellets by simultaneously dispensing the desired number of droplets onto the solid, flat surface, freezing the droplets and lyophilizing the frozen droplets. Pellets prepared by this process from a liquid formulation may have a high concentration of a biological material (such as a protein therapeutic) and may be combined into a set of dried pellets.

In some embodiments, the solid, flat surface is the top surface of a metal plate which comprises a bottom surface that is in physical contact with a heat sink adapted to maintain the top surface of the metal plate at a temperature of −90° C. or below. Since the top surface of the metal plate is well below the freezing point of the liquid formulation, the droplet freezes essentially instantaneously with the bottom surface of the droplet touching the top surface of the metal plate.

In other embodiments, the solid, flat surface is hydrophobic and comprises the top surface of a thin film that is maintained above 0° C. during the dispensing step. The dispensed droplet is frozen by cooling the thin film to a temperature below the freezing temperature of the formulation.

Separating water from the unitary forms which are formed either on a solid element containing cavities or on a flat surface, can be performed by drying the unitary forms under conduction-dominant drying (using sublimation), radiant-dominant drying (using a microwave), or a combination thereof. In some embodiments, the unitary forms are dried under conduction-dominant drying. In other embodiments, the unitary forms are dried under radiant dominant drying.

VI. Polymeric Coating Processes

In the processes of the present invention, the lyospheres are typically spray- or dip-coated with the enteric polymer coating composition. Preferably, the coating step comprises spray-coating the lyospheres with the enteric polymer coating composition. The desired weight gain can be determined by sampling the lyospheres and determining the actual weight gain of the coated lyospheres in comparison to the uncoated lyospheres.

A fluid bed process can be employed to uniformly coat individual lyospheres. The process includes providing a spray nozzle at the bottom of a fluidized bed of solid lyospheres. The lyospheres move with a fluidizing air stream that is designed to induce a cyclic particle flow upward past the spray nozzle. The nozzle sprays atomized droplets of the enteric polymer coating solution or suspension concurrently with particle flow. Passing particles move upward into an expansion chamber as film coat droplets deposit on their surfaces. The expansion chamber reduces air velocity to allow particles to circulate back to the coating chamber. It also allows particles to further separate from one another temporarily and minimize the potential for lyosphere agglomeration and accretion. The organic solvent or aqueous coating vehicle evaporates as the particles move into and through the expansion chamber to leave a non-volatile part formulation ingredients on the lyosphere surface as part of the developing film coat. Process parameters are set to achieve optimal film coat characteristics. This batch process continues until each lyosphere is coated uniformly to the desired coat percentage or film thickness.

In some embodiments a bottom spray Wurster process is used to coat the lyospheres. This fluid-bed process for coating provides excellent coating uniformity and efficiency. This process has a product chamber containing an air distribution plate and a partition that together organize fluidization of the lyospheres through the partition (coating zone). The nozzle is mounted at the bottom of the product container and is centered in the coating zone. The short distances between the coating materials and lyospheres during the coating process minimize spray-drying and contribute to high coating uniformity and coating efficiency. This processing option uses the energies and controls of the fluid bed to create a pneumatic mass transport inside a special insert, which consists of a perforated bottom screen. Most of the process air is channeled through the center via a tube (Wurster column) to result in a Venturi effect, which sucks the product from outside the partition past the spray nozzle. In some embodiments the Wurster column can be replaced with a central rotating cone around which the particles move during product fluidization. Leaving the cylindrical partition and entering the conical expansion chamber the particle velocity is dramatically reduced. Excess moisture is rapidly evaporated in this assembly with the dry product returning repeatedly through the coating zone to receive more coating material.

The coated lyospheres can be filled into capsules/sachets using standard automated capsule or sachet filling equipment designed for filling pellets and sealing the capsules or sachets to accommodate the specified dose in the dosage form. Alternatively, the coated lyospheres can be bulk packaged into high density polyethylene bottles.

EXAMPLES

The following examples are provided to more clearly describe the present invention and should not be construed to limit the scope of the invention.

Example 1. Preparation and of an Enterically Coated Lyosphere Containing Myoglobin (Mb), Assessment of Coating Weight Gain, Bead Integrity and Oxidative Function This example demonstrates the process of the present invention as applied to a protein. In this example, myoglobin (Mb) served as the model protein.

Preparation

A high-throughput custom liquid handler (Biomek® FX from Beckman-Coulter, Brea, Calif.) was used to prepare frozen beads using myoglobin (Mb) as a model protein. Mb beads were prepared at 2 mg/mL concentration in 14% trehalose, 7% HPMC. The frozen beads were then transferred to a precooled shelf at −50° C., and the beads were dried according the procedure listed below;
 a. Extra Freeze: −50° C. with a hold time of 30 min; Condenser temperature of −50° C. and vacuum of 30 mTorr;
 b. Drying:
  (i) Step 1: −50° C. with a ramp time of 0 min and hold time of 120 min at 30 mTorr pressure;
  (ii) Step 2: 15° C. with a ramp time of 100 min and hold time of 1440 min at 30 mTorr pressure; and
  (iii) Step 3: 30° C. with a ramp time of 30 min and hold time of 300 min at 30 mTorr pressure.

After drying, the beads were subjected to a coating process as described below.

The coating was performed in a Mini-Glatt fluid bed coating equipment (Glatt Technologies, Ramsey, N.J.) using bottom spray with a Wurster column or by using using diskjet technology without the Wurster column (Solidlab 2 fluid bed systems from Robert Bosch Technology Inc.). Polymer for functional coating: 90% EUDRAGIT FS 30 D; 10% EUDRAGIT L30 D-55

| Material | Quantity (g) |
|---|---|
| EUDRAGIT FS 30D | 66.55 |
| PLASACRYL T20 | 9.98 |
| EUDRAGIT L 30 D-55 | 6.95 |
| PLASACRYL HTP20 | 1.78 |
| Water | 36.74 |
| Total suspension | 122.0 |
| Solid content | 20.0% |

Coating solution preparation: The individual excipients were weighed as outlined above. EUDRAGIT FS 30 D was added to PLASACRYL T20 with continuous mixing using an agitator for 5 mins. EUDRAGIT L 30 D-55 was subsequently added along with a fraction of the water to the above solution while continuing stirring for an additional 5 mins. Finally, PLASACRYL HTP20 was added with the remaining water and the mixture was stirred for an additional 10 mins. The coating solution was finally screened through a 50-mesh screen before spraying.

The fluid bed was preheated to an inlet air temperature of 25° C. prior to start of the run.

Process parameters for Mini-Glatt during batch run (Batch size 1-5 g)
   Nozzle diameter: 0.5 mm
   Air flow: 0.15-0.20 bars
   Spray rate: 1.5-2.0 g/min
   Product temperature: 22-26° C.
   Atomization pressure: 0.5-0.6 bars Process Parameters for SolidLab 2 during batch run (125 g-250 g)
   Inlet air humidity: 6 g/kg (at start of run to reduce static) to 1 g/kg for the course of the run
   Microclimate: 0.1 bar
   Nozzle diameter: 1.0 mm
   Air flow: 65-100 cfm
   Spray rate: at the start of the process to 5-15 g/min/gun
   Product temperature: 20-25° C.
   Atomization pressure: 0.5-0.6 bar Assessment of the Coating Weight Gain and Protein Recovery The coating weight gain was determined by stopping the coating process at specific time intervals, and weighing 20 beads to determine the actual weight gain during the coating process compared to the uncoated lyospheres. Further coating was continued or discontinued depending on whether the target weight gain was achieved or not. The lyospheres were subsequently dried for 1-2 min post coating after stopping the spraying of the coating solution. Alternatively, with the larger batch, the weight gain was determined based on the theoretical amount of solids sprayed onto the lyospheres with the coating stopped after spraying the requisite amount of coating solution for a pre-determined weight gain. At the end of the spraying, Aerosil (fumed silica) was optionally added to water at 10% w/w and sprayed onto the pellets to avoid any stickiness during storage.

Figure 1B:
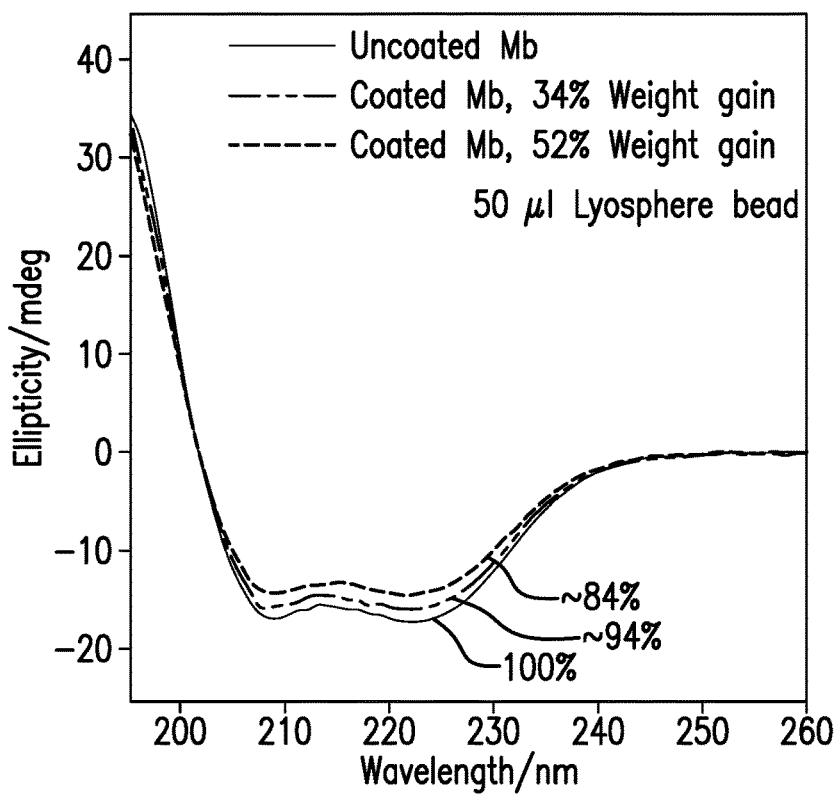
FIG. 1B shows the recovery of secondary structure of myoglobin from enterically-coated lyospheres as measured by circular dichroism following dissolution in 10 mM phosphate buffered saline, pH 7.4 in comparison with uncoated myoglobin.

The dried coated beads were characterized for their weight gain, and their concentrations were determined post dissolution in 10 mM PBS buffer pH 7.4 using UV-Vis spectroscopy. Secondary structure concentration was determined using Circular Dichroism (CD) (FIGS. 1A and 1B, respectively). As shown in FIG. 1A, a significant amount of yield recovery was observed by comparing the Mb concentration, as determined using absorbance at 410 nm. Absorbance at 410 nm is indicative of the presence of heme in the heme pocket of Mb. Uncoated beads were used as the control. Concentration, as determined using absorbance at 410 nm and an extinction coefficient of 179,000 cm$^{-1}$M$^{-1}$, suggested a high percentage recovery for coated Mb (FIG. 1A, ~109% and ~94% recovery for 34% and 52% weight gains, respectively). It should be noted that the presence of polymer in the solution interferes with the UV baseline and thus, the recoveries obtained should be used with caution. A significant amount of secondary structure was retained in the coated beads, based on comparing the double minima at 208 and 222 nm in the CD spectra, suggesting that the lyosphere formulations thus obtained were amenable to the coating process. Secondary structure, as determined using CD, also suggests a significant amount of structure for the coated Mb (FIG. 1B, approx. 94% for 34% weight gain and approx. 84% for 52% weight gain).

Bead Integrity Assessment

Figure 2:
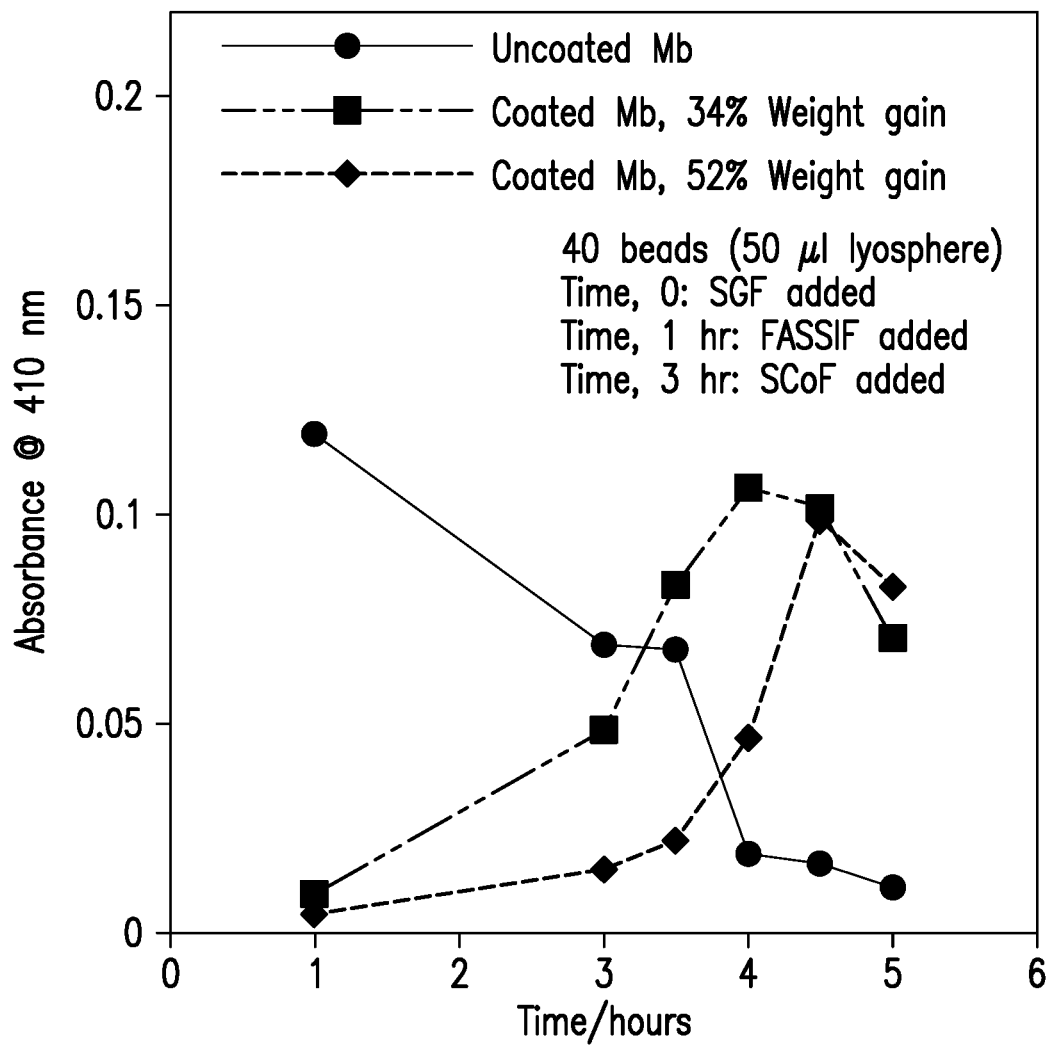
FIG. 2 shows the dissolution behavior and release of myoglobin from enterically-coated lyospheres as measured by UV-Vis spectroscopy at, 410 nm, over time, as the lyospheres were incubated in SGF, followed by FASSIF, and SCoF.

The beads were also tested for their bead integrity during dissolution in simulated gastric fluid (SGF, pH 1.8) and fasted simulated small intestine fluid (FASSIF, final pH 6.5) followed by dissolution in simulated colonic fluid (SCoF, final pH 7.2). Specifically, the experimental setup involved a multi-stage dissolution study using 100 mL dissolution vessels with paddles. Briefly, 40 lyosphere beads were placed in a sinker and immersed in 30 mL of SGF followed by addition of 10 mL of FaSSIF media to determine lyosphere dissolution for up to 1 and 2 hrs in SGF and FaSSIF, respectively. Finally, 10 mL of SCoF (simulated colonic fluid) was added to the existing media in the dissolution vessel to result in a final pH of 7.2 and to assess Mb release in SCoF for up to 2 hrs. After addition of each of the fluids, UV-Vis absorbance was collected using a 1 cm path length quartz cuvette. The results suggest that at higher weight gains (52% weight gain, FIG. 2), the bead integrity was maintained even after the addition of SGF and FASSIF fluid and a significant amount of active (Mb) was released only upon addition of SCoF (>80%, FIG. 2). Please note that, in contrast to coated beads, uncoated Mb beads dissolved instantaneously upon addition of SGF, and precipitated out of solution over time.

As mentioned above, absorbance at 410 nm is indicative of the presence of heme in the heme pocket of Mb. These data suggest that higher polymer weight gains prevent premature protein release and degradation in simulated gastric fluid and simulated intestinal fluid (pH 6.5) in comparison to uncoated or lower weight gain-coated beads.

Assessment of Oxidative Function of Mb from the Coated Lyospheres

Figure 3A:
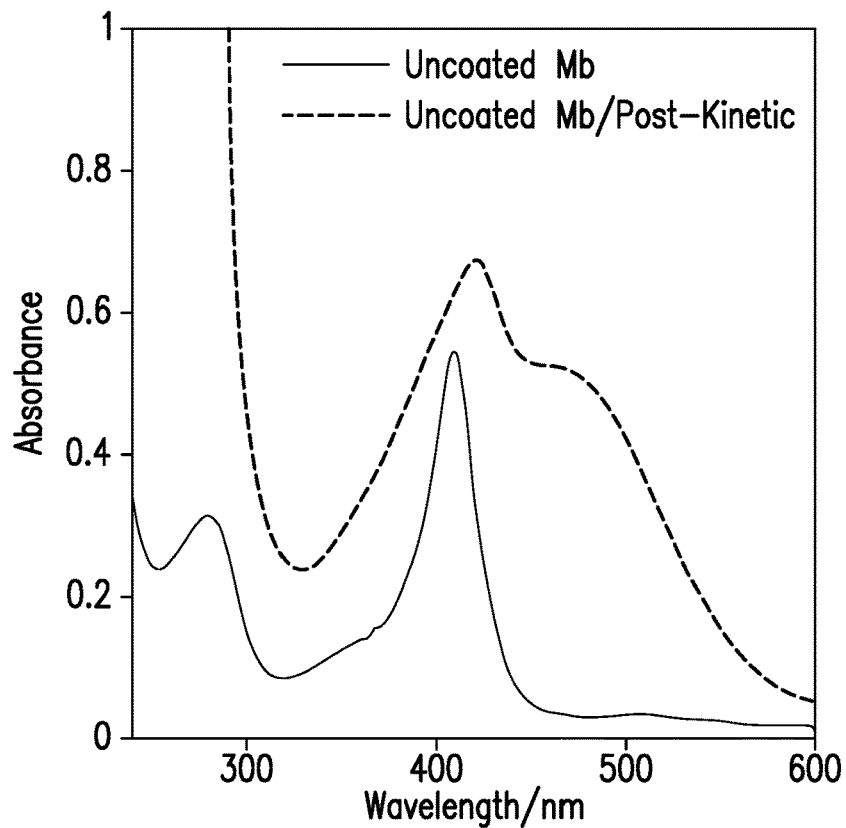
FIG. 3A shows the ability of myoglobin's oxidative ability to oxidize the substrate guiacol in the present of hydrogen peroxide as measured by UV-Vis spectroscopy.
Figure 3B:
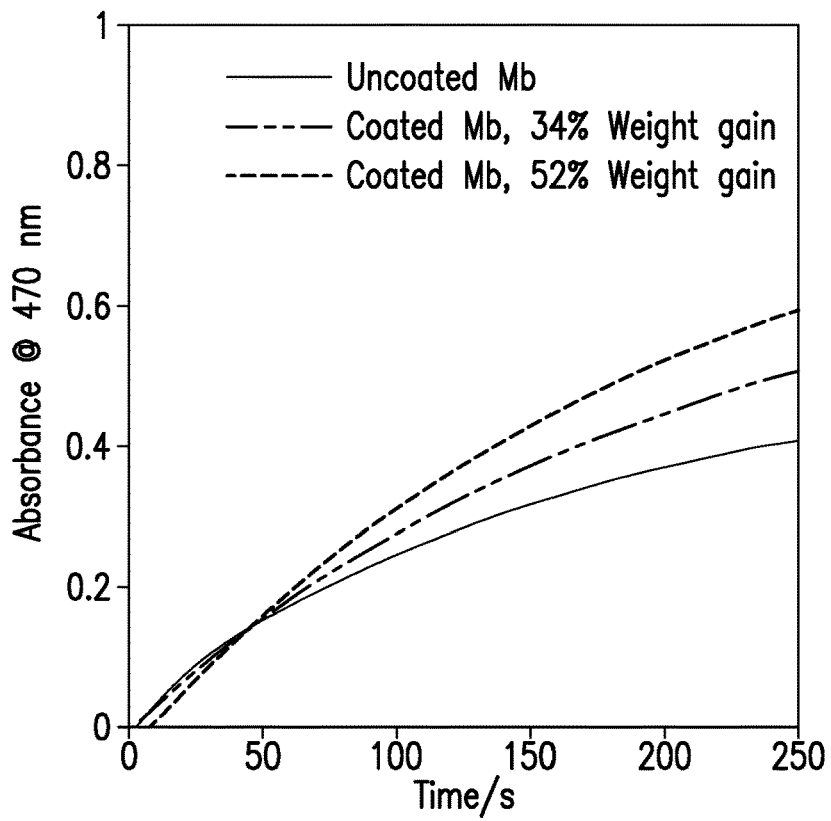
FIG. 3B shows myoglobin's ability to convert the substrate guiacol to a colored product in the presence of hydrogen peroxide as measured by UV-Vis spectroscopy from enterically-coated lyospheres following dissolution in simulated gastric fluid (SGF), followed by fasted simulated small intestinal fluid (FASSIF), and simulated colonic fluid (SCoF).

Although Mb is not an enzyme in the biological system, the ability of Mb to oxidize a number of substrates such as o-methoxyphenol (guaiacol), in the presence of hydrogen peroxide is known in the literature. Oxidation of guaiacol results in a colored product with an absorbance maximum around 470 nm, providing a convenient handle to monitor Mb activity in real time (FIG. 3A). Mb activity in uncoated and coated beads (34% and 52% weight gain, respectively) was followed by monitoring absorbance at 470 nm (FIG. 3B). These assays indicated a rapid increase in product formation over time. The initial rates (as measured using the first 60 data points) for uncoated and coated Mb along with their respective concentrations are shown in Table 1. The initial enzymatic rate showed an apparent increase from $2.79 \times 10^{-3}$/s (for uncoated Mb) to $3.23$-$3.33 \times 10^{-3}$/s for coated beads, indicative of heme functionality being maintained in the Mb coated beads. Although the results suggest an increase in enzymatic activity after coating, the increase was small and probably within assay variability. The assay variability (Table 1) was ~5% for uncoated beads and ~9% for coated beads. It is also possible that the polymer interferes with the absorbance baseline. Nevertheless, the dissolution study (FIG. 2) along with the activity data (FIG. 3B and Table 1) suggest that the coating process not only protected bead integrity during dissolution in simulated gastric fluid and simulated small intestine fluid but also preserved the functionality of Mb.

TABLE 1

Initial rate, calculated from first 60 data points, suggest comparable activity for the coated beads and were slightly better than the rates for uncoated beads.

|  | Uncoated Mb | Coated Mb (34% weight gain) | Coated Mb (52% weight gain) |
|---|---|---|---|
| Concentration (measured by UV-Vis) | 3.12 ± 0.11 µM | 3.39 ± 0.03 µM | 2.92 ± 0.01 µM |
| Initial Rate (first 60 data point) | 2.79 ± 0.14 (×10$^{-3}$/s) | 3.23 ± 0.28 (×10$^{-3}$/s) | 3.33 ± 0.15 (×10$^{-3}$/s) |
| % RSD (activity) | 5.02% | 8.67% | 4.5% |

Example 2. Preparation, Dissolution Behavior of an Enterically Coated Lyosphere Containing Anti-Thymic Stromal Lymphopoietin (TSLP) mAb This example demonstrates the process of the present invention as applied to an antibody. In this example, anti-TSLP mAb served as the model antibody. A description of the anti-TSLP antibody can be found in U.S. Pat. No. 8,637,019. The heavy (SEQ ID No.1) and light chain (SEQ ID No. 2) sequences of the anti-TSLP antibody are set forth in the sequence listings.

Preparation

As described above, a high-throughput custom liquid handler (Biomek® FX) was used to prepare frozen 50 µL active beads of model antibody formulation consisting of 10 mg/mL of anti-TSLP mAb. Specifically, the formulations consisted of 10 mg/mL anti-TSLP mAb in 14% trehalose, 7% HPMC, 1.50% sucrose, 2.13 mM histidine, 0.004% PS-80. The frozen beads were then transferred to a pre-cooled shelf at −50° C. and the beads were dried using the conditions listed below:
  a. Extra Freeze: −50° C. shelf; Condenser temperature of −50° C. and vacuum of 30 mTorr
  b. Drying:
    (i) Step 1: Hold at −50° C. for 30 min at 30 mTorr pressure
    (ii) Step 2: Ramp to 15° C. at a rate of 0.4° C./min and hold for 1440 min at 30 mTorr pressure
    (iii) Step 3: Ramp to 30° C. at a ramp rate of 0.2° C./min and hold time for 300 min at 30 mTorr pressure Post-drying, the beads were transferred to a NALGENE bottle and stored at 2-8° C. until further processing.

Post-drying, the beads were subjected to a coating process as described below.

The coating was performed in a Mini-Glatt fluid bed coating equipment using bottom spray with Wurster column.

Coating solution composition: 10% EUDRAGIT L30 D-55; 90% EUDRAGIT FS 30 D (for preparing the US coated lyospheres)

| Material | Quantity (g) |
|---|---|
| EUDRAGIT FS 30D | 66.55 |
| PLASACRYL T20 | 9.98 |
| EUDRAGIT L 30 D-55 | 6.95 |
| PLASACRYL HTP20 | 1.78 |
| Water | 36.74 |
| Total suspension | 122.0 g |
| Solid content | 20.0% |

Coating solution preparation: The individual excipients were weighed as outlined above. EUDRAGIT FS 30 D was added to PLASACRYL T20 with continuous mixing using an agitator for 5 min. EUDRAGIT L 30 D-55 was subsequently added along with water to the above solution while continuing stirring for additional 5 min. Finally, PLASACRYL HTP20 was added with the remaining water and stirred for additional 10 min. The coating solution was finally screened through a 50-mesh screen before spraying.

Coating solution composition: 100% EUDRAGIT FS 30 D (for preparing the S-coated lyospheres)

| Material | Quantity (g) |
|---|---|
| EUDRAGIT FS 30D | 60.61 |
| PlasACRYL T20 | 9.09 |
| Water | 30.30 |
| Total suspension | 100.0 g |
| Solid content | 20.0% |

Coating solution preparation: The individual excipients were weighed as outlined above. PLASACRYL T20 was shaken before use. The outlined amounts of EUDRAGIT dispersion and water are added into the PLASACRYL T20 suspension and stirred for 10 minutes using a propeller stirrer. The coating solution was finally screened through a 50-mesh screen before spraying.

The fluid bed was preheated to an inlet air temperature of 25° C. prior to start of the run.

Process parameters for Mini-Glatt during batch run
Nozzle diameter: 0.5 mm
Air flow: 0.15-0.20 bars
Spray rate: 1.5-2.0 g/min
Product temperature: 21-25° C. for EUDRAGIT FS30D (100%) and 25-30° C. for EUDRAGIT FD30D/L30D
Atomization pressure: 0.5-0.7 bars Assessment of the Coating Weight Gain The coating weight gain was determined by stopping the coating process at specific time intervals, and weighing n=20 beads to determine the actual weight gain during the coating process compared to the uncoated lyospheres. Further coating was continued depending on whether the target weight gain was achieved or not. This measurement was also compared against the theoretical values obtained based on the amount of coating solution sprayed onto the beads on the basis of solid content in the coating solution. The lyospheres were subsequently dried in the fluid bed for ~2-4 minutes post coating after stopping the spraying of the coating solution. One batch of coated lyospheres (L'S coated WG1) had lyospheres with a 96% weight gain, while the other (S coated WG4) had coated lyospheres with a 100% weight gain.

Bead Integrity and Lyosphere Dissolution Assessments

A brief description of the method for determining the dissolution properties of the lyospheres is provided below. Specifically, the experimental setup involved a multi-stage dissolution study using 100 mL dissolution vessels with paddles. Briefly, 10 units of lyospheres were placed in a sinker and immersed in 30 mL of SGF followed by addition of 10 mL of FaSSIF media to determine lyosphere dissolution for up to 1 and 2 h respectively in SGF and FaSSIF. Finally, 10 mL of SCoF was added to the existing media in the dissolution vessel to result in a final pH of 7.2. Drug release in SCoF was assessed for up to 24 hrs.

Figure 4:
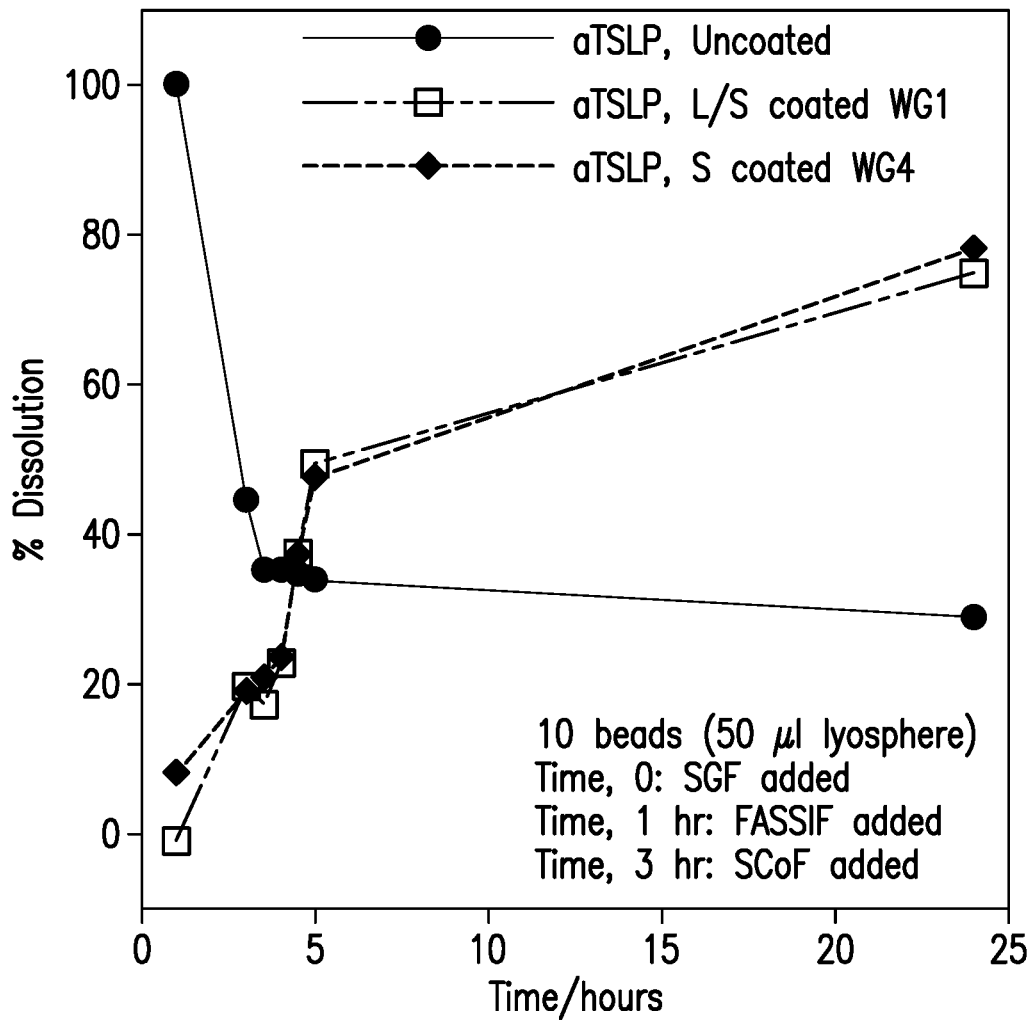
FIG. 4 is plot of the percentage dissolution of anti-TSLP mAb from enterically-coated lyospheres, over time, as the lyospheres were incubated in SGF, followed by FASSIF, and SCoF as compared with uncoated anti-TSLP mAb.

FIG. 4 is a plot of the percentage of drug dissolved as a function of time. The uncoated lysospheres (aTSLP, Uncoated) released all the drug in SGF and the drug concentration steadily decreases in FaSSIF and SCoF with possible degradation (e.g., unfolding aggregation, etc.) due to lack of enteric polymer protection. In contrast, the enterically coated lyospheres, with EUDRAGIT FS30D/L30D-55 (US coated WG1) or EUDRAGIT FS30D (S coated WG4), resulted in minimal drug release in SGF and <20% release in FaSSIF with the remaining drug being released over the next 24 h and beyond.

Uncoated samples were dispersed completely in SGF at the end of first hour, but coated samples were intact, demonstrating preservation of the functional coat preventing pre-mature release of the drug. In FaSSIF, L'S coated WG1 and S coated WG4 samples remain intact in contrast in FASSIF as demonstrated with <20% drug release in FaSSIF. The coated samples began to disperse in colonic media, and all were completely dispersed at the 24 h time point as shown in FIG. 4.

Determination of Protein Concentration and Secondary Structure Following Dissolution of the Coated Lyospheres Post-coating, the 10 mg/mL beads with the 45.8% weight gain were characterized for protein concentration using UV-Vis spectroscopy and secondary structure using circular dichroism (CD). For comparison, frozen liquid beads and uncoated beads were also characterized.

For these analyses, a total of 20 beads for each were placed in 20 mL of 0.01 M PBS, pH 7.4 (final anti-TSLP mAb concentration of approx. 0.5 mg/mL) and allowed to dissolve overnight at 2-8° C. followed by 4 hours at 37° C. UV absorbance at 280 nm ($Abs_{280\ nm}$) was measured using an Agilent UV-Vis spectrometer (see Table 2 below). There was no significant difference in $Abs_{280\ nm}$ for the coated and the uncoated beads compared to the frozen beads and the liquid control. This result shows that there was no significant protein lost during the drying process, the coating process, and any handling steps.

TABLE 2

UV/Vis determination for enteric coated anti-TSLP mAb

| Formulations | Absorbance at 280 nm |
| --- | --- |
| liquid control (4° C.) | 0.80749 |
| frozen beads (−70° C.) | 0.82601 |
| uncoated bead | 0.81910 |

TABLE 2-continued

UV/Vis determination for enteric coated anti-TSLP mAb

| Formulations | Absorbance at 280 nm |
| --- | --- |
| coated bead | 0.83624 |
| uncoated yield (%) | 99.163 |
| coated yield (%) | 101.24 |
| loss during coating | no significant loss |

Figure 5:
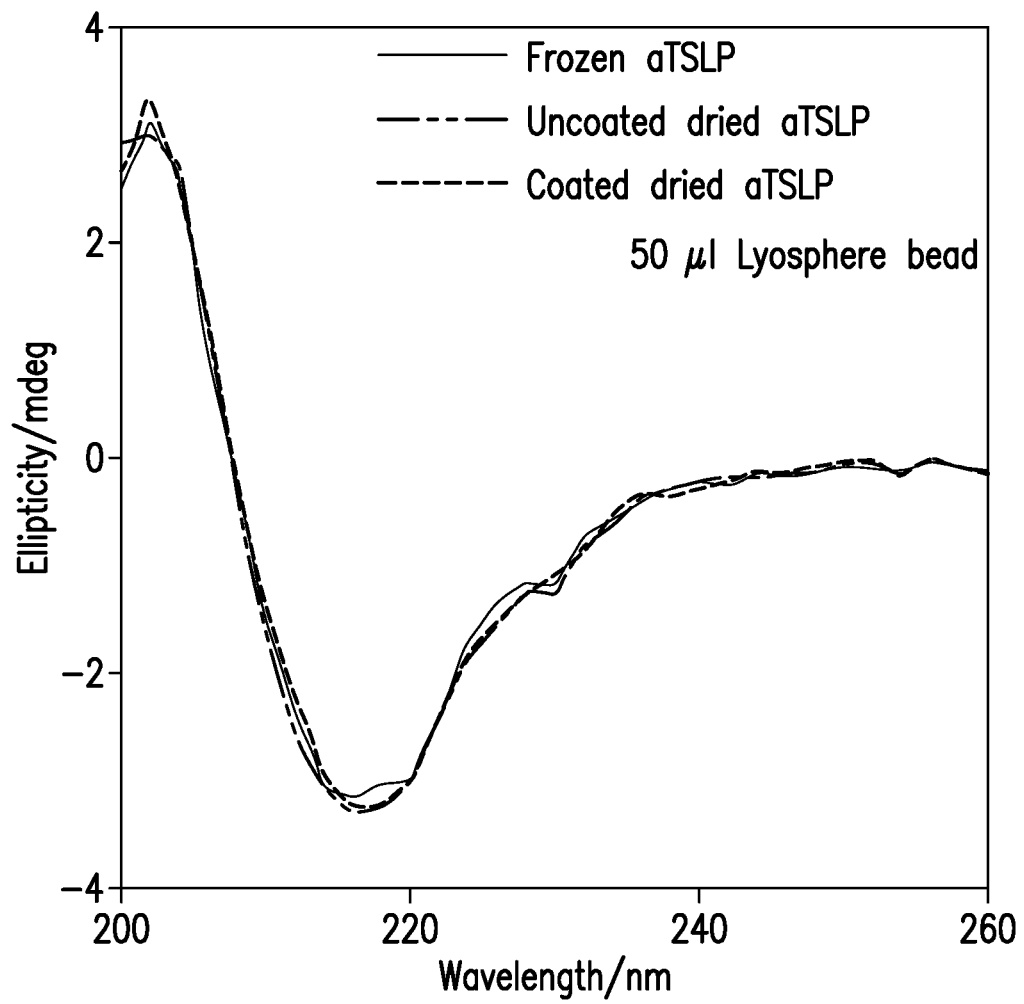
FIG. 5 shows the recovery of secondary structure of anti-TSLP mAb from enterically coated lyospheres (with 45.8% weight game) as measured by circular dichroism following dissolution in 10 mM phosphate buffered saline, pH 7.4 in comparison with uncoated as well as frozen anti-TSLP mAb.

CD spectra of the coated beads compared to the uncoated dried beads and the liquid frozen beads are shown in FIG. 5. CD spectra were measured for samples described above that had been diluted to a concentration of 0.1 mg/mL anti-TSLP mAb. Data were collected in the range of 200-260 nm using a 0.1 cm path length cuvette. Continuous scanning at 20 nm/min was used with a band width of 2 nm. No significant differences were observed in the CD absorbance suggesting that the coating and handling processes had no significant effect on the secondary structure of anti-TSLP mAb.

Example 3. Preparation and Dissolution Behavior of an Enterically Coated Lyosphere Containing Anti-Human Programmed Death Receptor (Anti-hPD-1) mAB This example demonstrates the process of the present invention as applied to an antibody. In this example, anti-hPD-1 mAb served as the model antibody. A description of the anti-hPD-1 mAb can be found in U.S. Pat. No. 8,354,509, the disclosure of which is hereby incorporated by reference as if fully set forth herein.

Preparation

As described above, a high-throughput custom liquid handler (Biomek® FX) was used to prepare frozen 50 µL active beads of model antibody formulation consisting of 5 mg/mL and 10 mg/mL of anti-hPD-1 mAb and anti-hPD-1 mAb, respectively. Specifically, the formulations consisted of 5 mg/mL anti-hPD-1 mAb in 14% trehalose, 7% HPMC, 1.4% sucrose, 2 mM histidine, 0.004% PS-80 or 10 mg/mL anti-hPD-1 mAb in 14% trehalose, 7% HPMC, 1.4% sucrose, 2 mM histidine, 0.004% PS-80. The frozen beads were then transferred to a precooled shelf at −50° C., and the beads were dried using the conditions listed below:

a. Extra Freeze: −50° C. shelf; Condenser temperature of −50° C. and vacuum of 30 mTorr b. Drying:
  (i) Step 1: Hold at −50° C. for 30 min at 30 mTorr pressure
  (ii) Step 2: 15° C. with a ramp rate of 0.4° C./min and hold time of 1440 min at 30 mTorr pressure
  (iii) Step 3: 30° C. with a ramp rate of 0.2° C./min and hold time of 300 min at 30 mTorr pressure Post-drying, the beads were transferred to a NALGENE bottle and stored at 2-8° C. until further processing.

Post-drying, the beads were subjected to a coating process as described below.

Coating solution composition: 10% EUDRAGIT L30 D-55; 90% EUDRAGIT FS 30 D (for preparing the L/S coated lyospheres)

| Material | Quantity (g) |
| --- | --- |
| EUDRAGIT FS 30D | 66.55 |
| PLASACRYL T20 | 9.98 |
| EUDRAGIT L 30 D-55 | 6.95 |

| Material | Quantity (g) |
| --- | --- |
| PLASACRYL HTP20 | 1.78 |
| Water | 36.74 |
| Total suspension | 122.0 g |
| Solid content | 20.0% |

Coating solution preparation: The individual excipients were weighed as outlined above. EUDRAGIT FS 30 D was added to PLASACRYL T20 with continuous mixing using an agitator for 5 mins. EUDRAGIT L 30 D-55 was subsequently added along with water to the above solution while continuing stirring for additional 5 min. Finally, PLASACRYL HTP20 was added with the remaining water, and the mixture was stirred for an additional 10 min. The coating solution was finally screened through a 50-mesh screen before spraying.

The fluid bed was pre heated to an inlet air temperature of 25° C. prior starting the run.

Process parameters for Mini-Glatt during batch run
Nozzle diameter: 0.5 mm
Air flow: 0.15-0.25 bars
Spray rate: 1.5-2.0 g/min
Product temperature: 25-30° C. for EUDRAGIT FD30D/L30D
Atomization pressure: 0.5-0.75 bars Assessment of the Coating Weight Gain The coating weight gain was determined by stopping the coating process at specific time intervals and weighing 20 beads to determine the actual weight gain during the coating process compared to the uncoated lyospheres. Further coating was applied depending on whether the target weight gain was achieved. This measurement was also compared against the theoretical amount of coating solution sprayed onto the beads based on the solid content in the coating solution. The lyospheres were subsequently dried in the fluid bed for ~2-4 minutes post coating after stopping the spraying of the coating solution. The coated lyospheres had a 61.4% weight gain.

Bead Integrity and Lyosphere Dissolution Assessments

Figure 6:
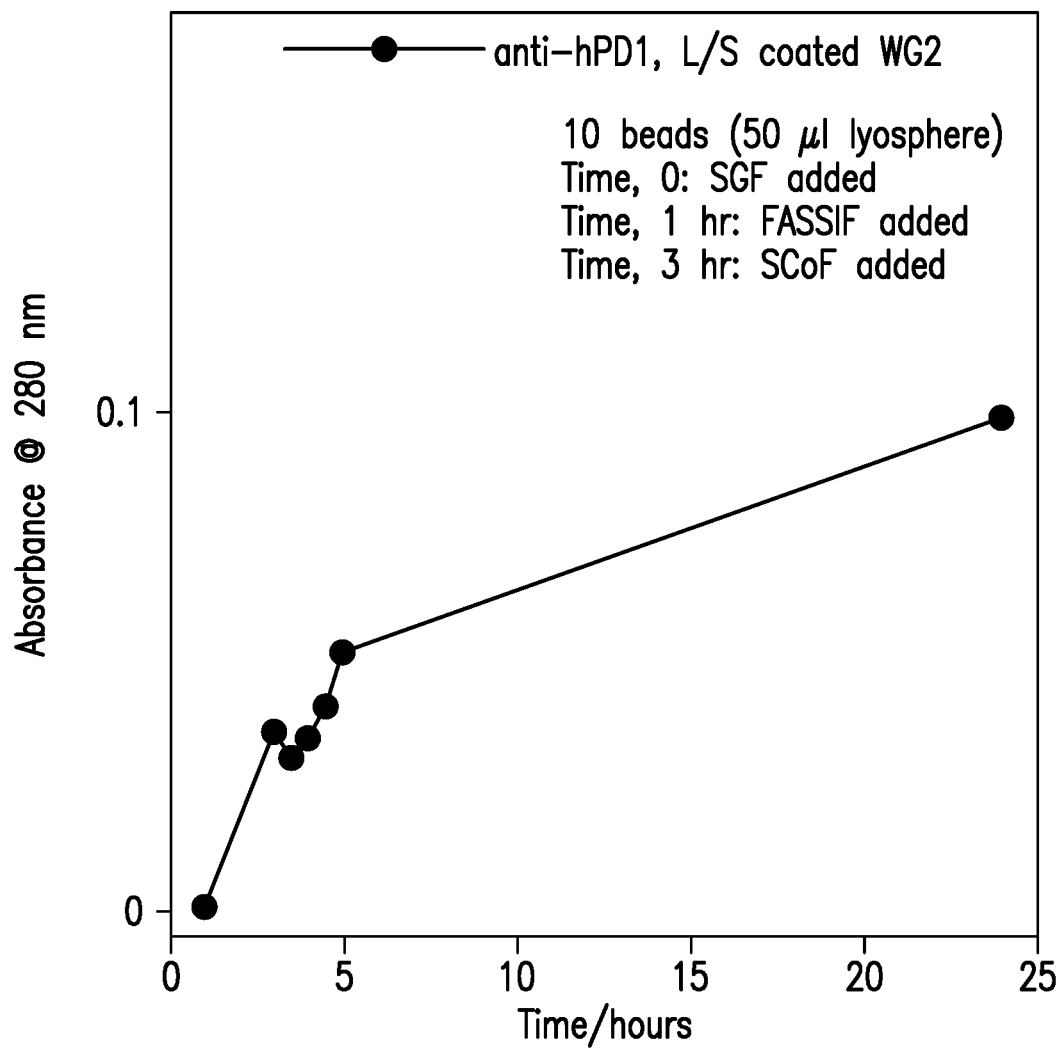
FIG. 6 shows the yield recovery of anti-hPD1 mAb from enterically-coated lyospheres as measured by UV-Vis spectroscopy at λ 280 nm, following incubation of the lyospheres in SGF, followed by FASSIF, and SCoF.

FIG. 6 is a plot of baseline corrected absorbance at 280 nm of anti-hPD1 mAb for polymer-coated lyospheres with EUDRAGIT L30D-55/FS30D (L/S coated WG2 in the figure) as monitored as a function of dissolution time. Initially, 10 beads (100 µL each with 5 mg/mL anti-hPD1 mAb) were dissolved in 30 mL of simulated gastric fluid (SGF, pH 1.8) and an absorbance spectrum was collected after 1 h of mixing. FASSIF media (10 mL) was added into the dissolution apparatus, and stirring was continued for 2 h. Subsequently, SCoF (10 mL) was added to the dissolution apparatus and the absorbance was monitored at every 30 min interval for the next 2 hours, followed by final sampling at the 24 hour time point.

The data suggest that functional coated lyospheres stayed intact and prevented premature protein release in SGF with drug release being triggered in FaSSIF, while the majority of the protein release occurs in SCoF (simulated colonic fluid).

Determination of Concentration and Secondary Structure Following Dissolution of the Coated Lyospheres Post-coating, the 10 mg/mL anti-hPD-1 mAb beads were characterized for protein concentration using UV-Vis spectroscopy and secondary structure using Circular Dichroism (CD). For comparison, frozen liquid beads and uncoated beads were also characterized.

For these analyses, a total of 20 beads for each were placed in 20 mL of 0.01 M PBS, pH 7.4 (final anti-hPD-1 mAb concentration of approximately 0.5 mg/mL) and allowed to dissolve overnight at 2-8° C. followed by 4 hours at 37° C. UV absorbance at 280 nm ($Abs_{280\ nm}$) was measured using an Agilent UV-Vis spectrometer (see Table 3 below). There was a loss of ~3-7% anti-hPD-1 mAb determined by $Abs_{280\ nm}$ for the uncoated and the coated beads compared to the frozen beads. This result shows that there was minimal protein lost during the drying process, the coating process, and the handling steps.

TABLE 3

UV/Vis determination for enteric coated anti-hPD-1 mAb

| Formulations | Absorbance at 280 nm |
| --- | --- |
| liquid control (4° C.) | 0.88427 |
| frozen beads (−70° C.) | 0.90847 |
| uncoated bead | 0.87969 |
| coated bead | 0.84579 |
| uncoated yield (%) | 96.832 |
| coated yield (%) | 93.100 |
| loss during coating | 3.85% |

Figure 7:
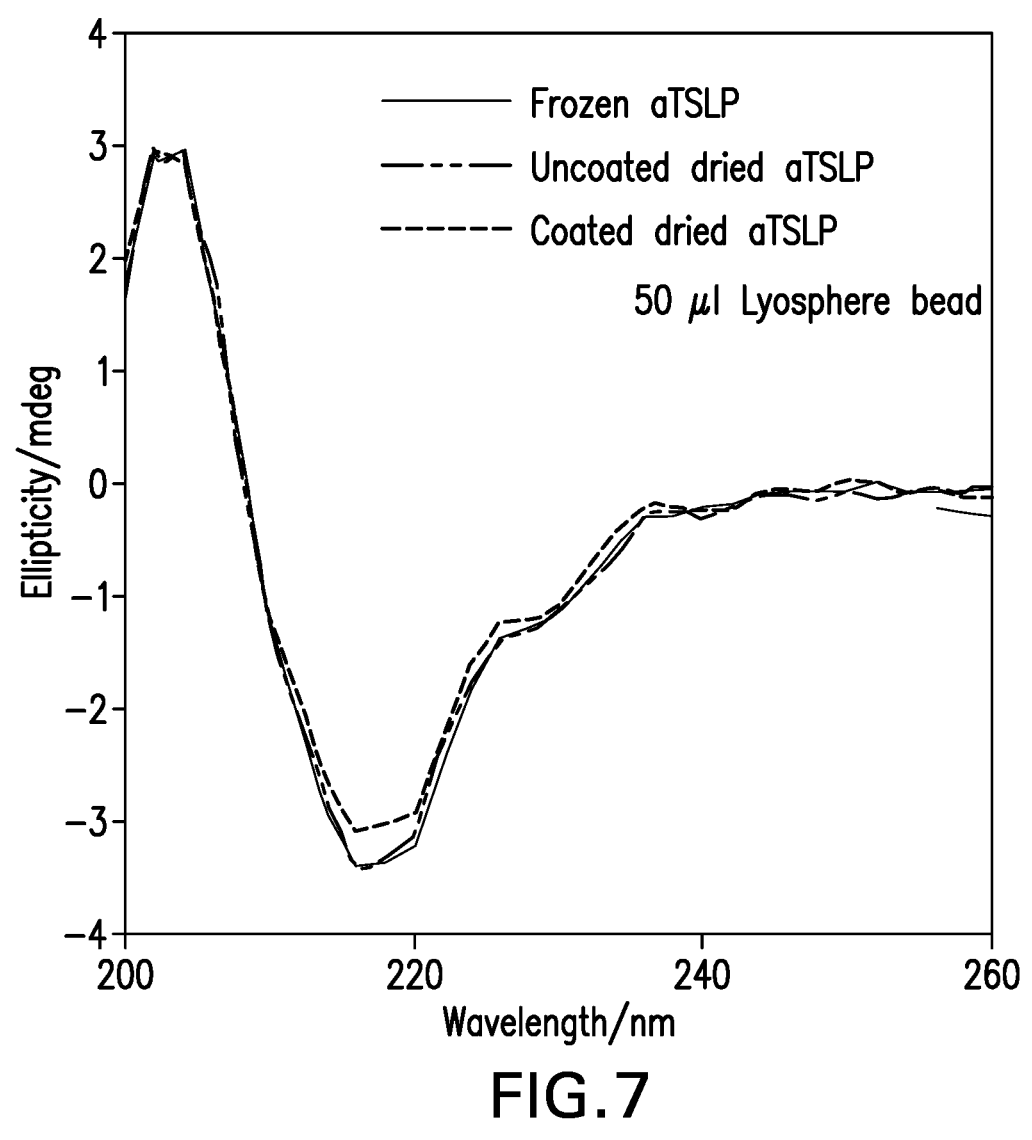

CD spectra of the coated beads compared to the uncoated dried beads and the liquid frozen beads are shown in FIG. 7. CD spectra was measured for samples described above that had been diluted to a concentration of 0.1 mg/mL anti-hPD-1 mAb. Data were collected in the range of 200-260 nm using a 0.1 cm path length cuvette. Continuous scanning at 20 nm/min was used with a band width of 2 nm. No significant differences were observed in the CD signal suggesting that the coating and handling processes had no significant effect on the secondary structure of anti-hPD-1 mAb.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

We claim:

1. A process for preparing enterically-coated lyospheres comprising a therapeutic agent comprising:
   a.) providing lyospheres comprising the therapeutic agent;
   b.) coating said lyospheres with an enteric polymer coating composition; and
   c.) isolating said enterically-coated lyospheres;
   wherein said lyospheres in step a.) are prepared by:
      mixing the therapeutic agent, a sugar, and a binding-gel forming agent in an aqueous medium to form an aqueous medium mixture;
      segregating the aqueous medium mixture into unitary volumes;
      freezing said unitary volumes to form unitary forms; and
      separating water from said unitary forms to yield the lyospheres.

2. The process of claim 1, wherein in step b.) the enteric polymer coating composition comprises an anionic polymer selected from an acrylic or methacrylic acid copolymer, a carboxylic acid-containing cellulosic polymer, a carboxylic acid-containing polyvinyl acetate copolymer, or shellac.

3. The process of the claim 2, wherein
   the acrylic or methacrylic acid copolymer is poly(methacrylic acid, methyl methacrylate) 1:1, poly(methacrylic acid, methyl methacrylate) 1:2, poly(methacrylic acid, ethyl acrylate) 1:1; or poly(methyl acrylate, methyl methacrylate, methacrylic acid) 7:3:1
   the carboxylic acid-containing cellulosic polymer is hydroxypropylmethyl cellulose phthalate, cellulose acetate phthalate (CAP), cellulose acetate trimellitate, hydroxypropylmethyl cellulose succinate; and the carboxylic acid-containing polyvinyl acetate copolymer is polyvinyl acetate phthalate.

4. The process of claim 1, wherein step b.) comprises spray- or dip-coating the lyospheres with the enteric polymer coating composition.

5. The process of claim 4, wherein said coating step b.) comprises spray-coating the lyospheres with the enteric polymer coating composition.

6. The process of claim 5, wherein said spray-coating is bottom spray-coating, tangential spray-coating, or pan-coating.

7. The process of claim 6, wherein said enteric polymer coating composition is dispersed in an aqueous medium.

8. The process of claim 1, wherein the coating and isolating steps result in enterically-coated lyospheres having a weight gain of at least 10 wt. %.

9. The process of claim 1, wherein said segregating, freezing, and separating steps comprise:

segregating the aqueous medium mixture into unitary volumes on a pre-cooled flat surface of a solid element to form the unitary forms;

removing the unitary forms from the flat surface, and drying the unitary forms under conduction- or radiant-dominant drying to yield said lyospheres.

10. The process of claim 1, wherein said segregating, freezing, and separating steps comprise:

filling cavities of a solid element with the aqueous medium mixture;

freezing the aqueous medium mixture while present in the cavities by extracting heat from the aqueous medium mixture through a cavity wall by conduction to form the unitary forms;

removing the unitary forms from the cavity, and drying the unitary forms in a vacuum to obtain the lyospheres.

11. The process of claim 1, wherein said binding-gel forming agent is a cellulosic polymer, polyvinylpyrollidone, starch, gelatin, polyethylene glycol, wax, a natural gum, a synthetic gum, or a combination thereof.

12. The process of claim 11, wherein said binding-gel forming agent is a cellulosic polymer selected from hydroxypropylmethyl cellulose, hydroxypropyl cellulose, methyl cellulose, microcrystalline cellulose, ethyl cellulose, or a combination thereof.

13. The process of claim 12, wherein said binding-gel forming agent is hydroxypropylmethyl cellulose.

14. The process of claim 1, wherein the therapeutic agent which is a polypeptide, a protein, a peptide, a lipopeptide, a glycoprotein, a fusion protein, a protein conjugate, a cytokine, an enzyme, an antibody, an oligonucleotide, a vaccine vector, small molecule, a live virus, an inactivated virus, a virus-like particle, a viral protein subunit, an adjuvant, microbiome, a prebiotic, probiotic, or an ectobiotic.

15. The process of claim 1, wherein said binding-gel forming agent comprises from 2 to 40% w/v of the aqueous medium mixture.

16. The process of claim 1, wherein said sugar is trehalose, sucrose, glucose, galactose, maltose, lactose, raffinose, fructose, saccharose, mannitol, sorbitol, xylitol, or a combination thereof.

17. The process of claim 16, wherein said sugar is trehalose.

18. The process of claim 16, wherein said sugar is a combination of trehalose and mannitol.

19. The process of claim 16, wherein said aqueous medium mixture comprises at least 8% w/v of the sugar.

20. The process of claim 1, wherein the sugar is trehalose and the binding-gel forming agent is hydroxypropylmethyl cellulose.

21. The process of the claim 20, wherein the ratio of trehalose to hydroxypropylmethylcellulose is from 10:1 to 1:5.

22. The process of claim 1, wherein said aqueous medium mixture is blended in the absence of gelatin.

* * * * *

SEQUENCE LISTING

```
<160> NUMBER OF SEQ ID NOS: 2

<210> SEQ ID NO 1
<211> LENGTH: 450
<212> TYPE: PRT
<213> ORGANISM: Artificial Sequence
<220> FEATURE:
<223> OTHER INFORMATION: Synthetic Polypeptide
```

<400> SEQUENCE: 1

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Ala Met His Trp Val Arg Gln Ala Pro Gly Gln Gly Leu Glu Trp Met
        35                  40                  45

Gly Thr Phe Ile Pro Leu Leu Asp Thr Ser Asp Tyr Ala Gln Lys Phe
    50                  55                  60

Gln Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Met Gly Val Thr His Ser Tyr Val Met Asp Ala Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Pro Ile Ser Ile Ser
            20                  25                  30

Val His Trp Tyr Gln Gln Lys Pro Gly Gln Ala Pro Arg Leu Leu Ile
        35                  40                  45

Tyr Phe Ala Ser Gln Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Thr Phe Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```